United States Patent [19]

Seizinger et al.

[11] Patent Number: 5,578,462
[45] Date of Patent: Nov. 26, 1996

[54] NF2 ISOFORMS

[75] Inventors: Bernd R. Seizinger, Stockton; Nikolai A. Kley; Albert B. Bianchi, both of Princeton, all of N.J.

[73] Assignee: Bristol-Myers Squibb Company, New York, N.Y.

[21] Appl. No.: 179,738

[22] Filed: Jan. 10, 1994

[51] Int. Cl.$^6$ .............................. C12P 21/06; C12N 5/00; C07K 1/00; C07H 19/00
[52] U.S. Cl. ................. 435/69.1; 435/240.2; 435/252.3; 435/320.1; 530/350; 536/22.1; 536/23.1; 536/23.5
[58] Field of Search ............................... 435/69.1, 240.2, 435/252.3, 320.1; 530/350; 536/22.1, 23.1, 23.5

[56] References Cited

PUBLICATIONS

Claudio et al. "Cloning of mouse Schwannomin . . . " 33rd Annual Meeting of Jn Soc. Cell Biol. Dec. 11–15, 1993.
Discher et al., Mechanochemistry of the alternatively spliced spectrin–actin binding domain in membrane skeletal protein 4.4, (1993) *J. Biol. Chem.* 268:7186–7195.
Fontaine et al., Parental origin of chromosome 22 loss in sporadic and NF2 neuromas, (1991) *Genomics* 10:280–283.
Luna et al., Cytoskeleton–plasma membrane interactions, (1992) *Science* 258:955–964.
Rouleau et al., Genetic linkage of bilateral acoustic neurofibromatosis to a DNA marker on chromosome 22, (1987) *Nature* 329:246–248.
Rouleau et al., Flanking markers bracket the neurofibromatosis type 2 (NF2) gene on chromosome 22, (1990) *Am. J. Hum. Genet.* 46:323–328.
Rouleau et al., Alteration in a new gene encoding a putative membrane–organizing protein causes neuro–fibromatosis type 2, (1993) *Nature* 363:515–521.
Seizinger et al., Loss of genes on chromosome 22 in tumorigenesis of human acoustic neuroma, (1986) *Nature* 322:644–647.
Seizinger et al., Common pathogenetic mechanism for three tumor types in bilateral acoustic neurofibromatosis, (1987) *Science* 236:317–319.
Seizinger et al., Molecular genetic approach to human meningioma: Loss of genes on chromosome 22, (1987) *Proc. Natl. Acad. Sci. USA* 84:5419–5423.
Seizinger et al., Report of the committee on chromosome and gene loss in human neoplasia, (1991) *Cytogenet. Cell Genet.* 58:1080–1096.
Trofatter et al., A novel moesin–, ezrin–, radixin–like gene is a candidate for the neurofibromatosis 2 tumor suppressor, (1993) *Cell* 72:791–800.
Wertelecki et al., Neurofibromatosis 2: Clinical and DNA linkage studies of a large kindred, (1988) *N. Engl. J. Med.* 319:278–283.
Wolff et al., Analysis of chromosome 22 deletions in neurofibromatosis type 2–related tumors, (1992) *Am. J. Hum. Genet.* 51:478–485.

*Primary Examiner*—Robert A. Wax
*Assistant Examiner*—Hyosuk Kim
*Attorney, Agent, or Firm*—Reed & Robins

[57] ABSTRACT

Novel human and mouse NF2 transcript isoforms and proteins encoded thereby, are disclosed. The isoforms are found in a variety of tissue and tumor types and represent differential processing of genomic DNA sequences, at the level of transcription, resulting in variant proteins. The isoforms provide useful tools for the analysis of the normal function of tumor suppressor factors, such as the merlin protein, and also provide useful markers for the detection of NF2 disease.

16 Claims, 17 Drawing Sheets

```
Mouse  601 GAT GAA GCT GAA ATG GAG TAT TTG AAG ATA GCT CAG GAC CTG GAG ATG TAT GGT GTG AAC 220
Mouse      Asp Glu Ala Glu Met Glu Tyr Leu Lys Ile Ala Gln Asp Leu Glu Met Tyr Gly Val Asn
Human       -   -   -   -   -   -   -   -   -   -   -   -   -   -   -   -   -   -   -   -

Mouse  661 TAC TTT ACA ATC CGG AAT AAA AAG GGC ACA GAG CTG CTT GGA GTG GAT GCT CTT GGG 240
Mouse      Tyr Phe Thr Ile Arg Asn Lys Lys Gly Thr Glu Leu Leu Gly Val Asp Ala Leu Gly
            Ala
Human       -   -   -   -   -   -   -   -   -   -   -   -   -   -   -   -   -   -   -

Mouse  721 CTT CAT ATC TAT GAC CCT GAG AAC AGG CTG ACC CCC AAG ATC TCC TTC CCA TGG AAT GAA 260
Mouse      Leu His Ile Tyr Asp Pro Glu Asn Arg Leu Thr Pro Lys Ile Ser Phe Pro Trp Asn Glu
Human       -   -   -   -   -   -   -   -   -   -   -   -   -   -   -   -   -   -   -   -

Mouse  781 ATC CGA AAC ATC TCC TAC AGC GAC AAG TTT ACT ATT AAA CCA CTG ATT CTT CAG GAT AAG AAG AAA ATT 280
Mouse      Ile Arg Asn Ile Ser Tyr Ser Asp Lys Phe Thr Ile Lys Pro Leu Ile Leu Gln Asp Lys Lys Ile
Human       -   -   -   -   -   -   -   -   -   -   -   -   -   -   -   -   -   -   -   -

Mouse  841 GAT GTC TTC AAC TCC TCA AAG CTT CGT GTT AAT AAG AAG CTG ATT CTT GAA CTA TGT 300
Mouse      Asp Val Phe Asn Ser Ser Lys Leu Arg Val Asn Lys Lys Leu Ile Leu Glu Leu Cys
Human       -   -   -   -   -   -   -   -   -   -   -   -   -   -   -   -   -   -   -

Mouse  901 ATT GGG AAC CAT GAC CTA TTT ATG AGG CGA AAA GCT GAC TCT TTA GAA AGG CAG CAG 320
Mouse      Ile Gly Asn His Asp Leu Phe Met Arg Arg Lys Ala Asp Ser Leu Glu Val Gln Gln
Human       -   -   -   -   -   -   -   -   -   -   -   -   -   -   -   -   -   -   -

Mouse  961 ATG AAA GCC CAG AGG GCC AGG GAA GAG AAG CAG ATG AAG CGG CTG GCT 340
Mouse      Met Lys Ala Gln Arg Ala Arg Glu Glu Lys Gln Met Glu Arg Leu Ala
Human       -   -   -   -   -   -   -   -   -   -   -   -   -   -   -   -

Mouse 1021 CGA GAG ATG AAG CGG ATG GAG GAG GCC CGT ACA AGA GAT GCT GAG TTA GAG AGG CTC 360
Mouse      Arg Glu Met Lys Arg Met Glu Glu Ala Arg Thr Arg Asp Ala Glu Leu Arg Leu
Human       -   -   -   -   -   -   -   -   -   -   -   -   -   -   -   -   -   -

Mouse 1081 CTG CAG AAA GAA GAA GCA ACG ATG AAT GCC AAT GAA GCT CTG CTG ATG CGC TCT GAG ACA 380
Mouse      Leu Gln Lys Glu Glu Ala Thr Met Asn Ala Asn Glu Ala Leu Met Arg Ser Glu Thr
Human       -   -   -   -   -   -   -   -   -   -   -   -   -   -   -   -   -   -   -

Mouse 1141 GCT GAT CTG GCT TTG GCT AAG CAG GAA GCT ATC ACA GAG GAG GAG GCC AAG CTT TTG GCA CAA 400
Mouse      Ala Asp Leu Ala Leu Ala Lys Gln Glu Ala Ile Thr Glu Glu Glu Ala Lys Leu Ala Gln
Human       -   -   -   -   -   -   -   -   -   -   -   -   -   -   -   -   -   -   -   -
```

```
Mouse  1201 AAG GCT GCA GAG GCT GAG CAA GAG ATG CAG CGA ATC AAG GCC ACG GCC ATT CGG ACA GAG  420
Mouse       Lys Ala Ala Glu Ala Glu Gln Glu Met Gln Arg Ile Lys Ala Thr Ala Ile Arg Thr Glu
Human Mouse  1261 GAG GAG AAG CGC CTG ATG GAG CAG CAG AAG GTG CTG GAA GCT GCA TTG CTG AAC ATG  440
Mouse       Glu Glu Lys Arg Leu Met Glu Gln Gln Lys Val Leu Glu Ala Ala Leu Leu Asn Met
Human                                                                              Lys Mouse  1321 GCT GAG GAG TCA GAG AGG AGG AGG AAG GCC AAG GCT GAT CAG TTA AAG CAA GAC TTG CAA GAA  460
Mouse       Ala Glu Glu Ser Glu Arg Arg Arg Lys Ala Ala Asp Gln Leu Lys Gln Asp Leu Gln Glu
Human Mouse  1381 GCC AGA GAA GCA GAA CGA GAG CGA AGA GCC AAG GCC AAG GCC ATC GCC AAG ACC CCC ACC  480
Mouse       Ala Arg Glu Ala Glu Arg Glu Arg Arg Ala Lys Ala Lys Ala Ile Ala Lys Thr Lys Pro Thr
Human Mouse  1441 TAT CCA AAC ATG CCA ATT CCA CCA CCT CCT TTA GAA CTC CTG ATA CCG AGC TTC GAC ATT  500
Mouse       Tyr Pro Asn Met Pro Ile Pro Pro Pro Pro Leu Glu Leu Leu Ile Pro Ser Phe Asp Ile
Human           Pro                 Ala                                              Asn Leu Mouse  1501 ATT GCT GAC AGC TTG TCA TTC GAC GAT ACG AAG GAC ATG AAG CGA CTT TCC ATG GAG  520
Mouse       Ile Ala Asp Ser Leu Ser Phe Asp Asp Thr Lys Asp Met Lys Arg Leu Ser Met Glu
Human       Gly Mouse  1561 ATA GAG AAA ACG GAA GTG GTG TAC ATG GAG GAG AAG AGC CTG CAG GAG CAG CTC AAC  540
Mouse       Ile Glu Lys Thr Glu Val Val Tyr Met Glu Glu Lys Ser Leu Gln Glu Gln Leu Asn
Human Mouse  1621 GAG CTC AAG ACG GAG ATC ATC GAG GCC TTG AAA CTC AAA CTC AAA GAG CGG CGA AAG GAG ACG GCC CTG GAC GTC  560
Mouse       Glu Leu Lys Thr Glu Ile Ile Glu Ala Leu Lys Leu Lys Leu Lys Glu Arg Arg Lys Glu Thr Ala Leu Asp Val
Human                                                                                                    Ile Mouse  1681 CTA CAC AGC GAG AGC TCA GAC AGA GGC GGG CCC AGC AGC AAG CAT AAT ACC ATT AAA AAG  580
Mouse       Leu His Ser Glu Ser Ser Asp Arg Gly Gly Pro Ser Ser Lys His Asn Thr Ile Lys Lys
Human           Asn     Asn Mouse  1741 CTC ACT CTG CAG AGC GCC TCC CGA GTG GCC TTC TTT GAA GAA CTC TAG caggtgacc-3'
Mouse       Leu Thr Leu Gln Ser Ala Lys Ser Arg Val Ala Phe Phe Glu Glu Leu *
Human                                                                       *
```

FIG. 1C

```
5'- gcgcccggtacctcgcg
  1 ATG GCC GGA GCC ATC GCT TCT CGC ATG AGC TCA CTC AAG AGG AAG CAG CCC AAG       20
    Met Ala Gly Ala Ile Ala Ser Arg Met Ser Ser Leu Lys Arg Lys Gln Pro Lys 61 ACA TTC ACG GTG CGG ATC GTC ACC TTC AGC TTC GAG GAC GCC ATG TGC GAG ATG AAA   40
    Thr Phe Thr Val Arg Ile Val Thr Phr Ser Phe Glu Asp Ala Met Cys Glu Met Lys 121 TGG AAG GGG AAG GAC CTG TTT GAT TTG GTG TGC CGG ACA CTG GGG CTT CGG GAA ACC TGG 60
    Trp Lys Gly Lys Asp Leu Phe Asp Leu Val Cys Arg Thr Leu Gly Leu Arg Glu Thr Trp 181 TTC TTT GGA CTG CAG TAT ACA ATC AAG GAC GTG GCC ACG TGG CTC AAA ATG GAC AAG AAG 80
    Phe Phe Gly Leu Gln Tyr Thr Ile Lys Asp Val Ala Thr Trp Leu Lys Met Asp Lys Lys 241 GTG GAT CAT GTT TCG AAG GAA GAA GTT CCA ACC TTT CAC CTG GCC AAA TTT           100
    Val Leu Asp His Asp Val Ser Lys Glu Glu Val Pro Thr Phe His Leu Ala Lys Phe 301 TAT CCT GAA AAT GCT GAG GAG CTA GTT CAA GAG ATC ACG TGC CAC CAC TTA TTT TTC TTA 120
    Tyr Pro Glu Asn Ala Glu Glu Leu Val Gln Glu Ile Thr Cys His His Leu Phe Phe Leu 361 CAG GTG AAG AAG ATT TTG GAT AAG GCC AAG TAT GAC TAT TGC CCT GAG GCG TCC GTG CTC 140
    Gln Val Lys Lys Ile Leu Asp Lys Ala Lys Tyr Asp Tyr Cys Pro Glu Ala Ser Val Leu 421 TTG GCG TCA TAT GCT GTC CAG GCC AAG TAT GGC GAC TAT CCC TCT GTG CAC CAG AAG CGG 160
    Leu Ala Ser Tyr Ala Val Gln Ala Lys Tyr Gly Asp Tyr Pro Ser Val His Lys Arg 481 GGA TTT TTA GCC CAA GAG GAA TTG CTC CCG ATA AAT CTC TAT CAG ATG ACT           180
    Gly Phe Leu Ala Gln Glu Glu Leu Leu Pro Lys Arg Ile Asn Leu Tyr Gln Met Thr 541 CCG GAA ATG TGG GAG AGA ATT ACG GCT TGG TAT CAG GAC CAC CGG ATG AGA GCC AGG     200
    Pro Glu Met Trp Glu Arg Ile Thr Ala Trp Tyr Gln Asp His Arg Met Arg Ala Arg 601 GAT GAA GCT GAA ATG GAG TAT TTG AAG ATA GCT CAG GAC CTG GAG CTG GGT GTG AAC    220
    Asp Glu Ala Glu Met Glu Tyr Leu Lys Ile Ala Gln Asp Leu Glu Leu Gly Val Asn 661 TAC TTT ACA ATC CGG AAT AAA AAG GGC ACA GAG TTG CTG CTT GGA GTG GAT GCT CTT GGG 240
    Tyr Phe Thr Ile Arg Asn Lys Lys Gly Thr Glu Leu Leu Leu Gly Val Asp Ala Leu Gly
```

FIG. 2A

```
721  CTT CAT ATC TAT GAC CCT GAG AAC AGG CTG ACC CCC AAG ATC TCC TTC CCA TGG AAT GAA  260
     Leu His Ile Tyr Asp Pro Glu Asn Arg Leu Thr Pro Lys Ile Ser Phe Pro Trp Asn Glu

781  ATC CGA AAC ATC TCC TAC AGC GAC AAG GAG TTT ACT ATT AAA CCA CTG GAT AAG AAA ATT  280
     Ile Arg Asn Ile Ser Tyr Ser Asp Lys Glu Phe Thr Ile Lys Pro Leu Asp Lys Lys Ile

841  GAT GTC TTC AAA TTT AAC TCC TCA AAG CTT CGT GTT AAT AAG CTG ATT CTT CAG CTA TGT  300
     Asp Val Phe Lys Phe Asn Ser Ser Lys Leu Arg Val Asn Lys Leu Ile Leu Gln Leu Cys

901  ATT GGG AAC CAT GAC CTA TTT ATG AGG CGA AAA GCT GAC TCT TTA GAA GTT CAG CAG  320
     Ile Gly Asn His Asp Leu Phe Met Arg Arg Lys Ala Asp Ser Leu Glu Val Gln Gln

961  ATG AAA GCC CAG GCC AGG GAA GAA AAG CAG GCT AGA ATG CAG AGG CGG CTG GCT  340
     Met Lys Ala Gln Ala Arg Glu Glu Lys Gln Ala Arg Met Gln Arg Leu Ala

1021 CGA GAG AAG ATG CGG GAG GCC ATG GAG GAG GCC GAG GAT GAG CTG ATG GAG GAG CTC  360
     Arg Glu Lys Met Arg Glu Ala Met Glu Glu Ala Glu Asp Glu Leu Met Glu Glu Leu

1081 CTG CAG ATG AAA GAA GAA GCA ACG ATC CAG ATC ACA CTG ATG CGC TCT GAG GAG ACA  380
     Leu Gln Met Lys Glu Glu Ala Thr Ile Gln Ile Thr Leu Met Arg Ser Glu Glu Thr

1141 GCT GAT CTG TTG GCT GCT GAA AAG CAA ATG GAG CAG CGA ATG AAG CTT TTG GCA CAA  400
     Ala Asp Leu Leu Ala Ala Glu Lys Gln Met Glu Gln Arg Met Lys Leu Leu Ala Gln

1201 AAG GCA GAG GCA GCT GAG ATG CAG CAG ATG GAG GTG CTG GCA ATT CGG ACA GAG  420
     Lys Ala Glu Ala Ala Glu Met Gln Gln Met Glu Val Leu Ala Ile Arg Thr Glu

1261 GAG AAG CGC ATG ATG CTG CAG GAG GTG CTG GCA TTG AAC ATG  440
     Glu Lys Arg Leu Met Leu Gln Glu Val Leu Ala Leu Asn Met

1321 GCT GAG TCA GAG AGG AGG GCT GAT CAG CAG TTA CAA GAC TTG CAA GAA  460
     Ala Glu Ser Glu Arg Arg Ala Asp Gln Gln Leu Gln Asp Leu Gln Glu

1381 GCC AGA GAA GCA CGA GAG AGA GCC CAG AAG CTC TTA GAA ATC GCC ACC CCC ACC  480
     Ala Arg Glu Ala Arg Glu Arg Ala Gln Lys Leu Leu Glu Ile Ala Thr Lys Pro Thr
```

*FIG. 2B*

```
1441  TAT CCA CCC ATG AAC CCA ATT CCA CCA CTG CCT CCT GAC ATA CCG AGC TTC GAC ATT
      Tyr Pro Pro Met Asn Pro Ile Pro Pro Leu Pro Pro Asp Ile Pro Ser Phe Asp Ile  500

1501  ATT GCT GAC AGC TTG TCA TTC GAC TTC AAG GAT ACG ATG CGA CTT TCC ATG GAG
      Ile Ala Asp Ser Leu Ser Phe Asp Phe Lys Asp Thr Met Arg Leu Ser Met Glu  520

1561  ATA GAG AAA GAA GTG TAC ATG AAA GAG AAG AGC CAC CTG CAG GAG CAG CTC AAC
      Ile Glu Lys Glu Val Tyr Met Lys Glu Lys Ser His Leu Gln Glu Gln Leu Asn  540

1621  GAG CTC AAG ACG GAG ATC GAG GCC TTG AAA CTC AAA GAG CGG GAG ACG GCC TTG GAC GTC
      Glu Leu Lys Thr Glu Ile Glu Ala Leu Lys Leu Lys Glu Arg Glu Thr Ala Leu Asp Val  560

1681  CTA CAC AGC AGC GAG AGC TCA GAC AGA GGC CCC AGC AGC AAG CAT AAT ACC ATT AAA AAG
      Leu His Ser Glu Ser Ser Asp Arg Gly Pro Ser Ser Lys His Asn Thr Ile Lys Lys  580

1741  CCT CAA GCC AGA AGA CCT ATC TGC ATT TGA GTC CTC AAA CTC ACT CTG CAG AGC
      Pro Gln Ala Arg Arg Pro Ile Cys Ile ***  591

1801  GCC AAG TCC CGA GTG GCC TTC TTT GAA GAA CTC TAGcaggtgacc-3'
```

```
                                5'- gcgcccggtacctcgcg
  1 ATG GCC GGA GCC ATC GCT TCT CGC ATG AGC TCA CTC AAG AGG AAG CAG CCC AAG
    Met Ala Gly Ala Ile Ala Ser Arg Met Ser Ser Leu Lys Arg Lys Gln Pro Lys    20

61 ACA TTC ACG GTG CGG ATC GTC ACC GTC ATG GAC GAG TCA CTC AAG AGG AAG CAG CCC AAG
    Thr Phe Thr Val Arg Ile Val Thr Met Asp Glu Met Glu Phe Asn Cys Glu Met Lys    40

121 TGG AAG GGG AAG GAC CTG TTT GAT TTG GTG TGC CGG ACA CTG GGG CTT CGG GAA ACC TGG
    Trp Lys Gly Lys Asp Leu Phe Asp Leu Val Cys Arg Thr Leu Gly Leu Arg Glu Thr Trp    60

181 TTC TTT GGA CTG CAG TAT ACA ATC AAG GAC GTG GCC TGG CTC AAA ATG GAC AAG AAG
    Phe Phe Gly Leu Gln Tyr Thr Ile Lys Asp Val Ala Trp Leu Lys Met Asp Lys Lys    80

241 GTG TTG GAT CAT CAT GTT TCG AAG GAA GAG CTA GAG GAG CCA GTT ACC TTT CAC CTG GCC AAA TTT
    Val Leu Asp His His Val Ser Lys Glu Glu Leu Glu Glu Pro Val Thr Phe His Leu Ala Lys Phe    100

301 TAT CCT GAA AAT GCT GAG GAG ATT TTG GAT GAA CAA CAC ATC ACG TTC CCT GAG GCG TCC GTG CTC
    Tyr Pro Glu Asn Ala Glu Glu Ile Leu Asp Glu Gln His Ile Thr Phe Pro Glu Ala Ser Val Leu    120

361 CAG GTG AAG GTG AAG AAG CAG GTC GTC CAG GCC TAT GGC GAC CCC TCT GTG CAC AAG CGG
    Gln Val Lys Val Lys Lys Gln Val Val Gln Ala Tyr Gly Asp Tyr Asp Pro Ser Val His Lys Arg    160

421 TTG GCG TCA TAT TAC AAG GTC GTC CAG GAA TTG CTC CCG ATA AAT CTC TAT CAG ATG ACT
    Leu Ala Ser Tyr Tyr Lys Val Ala Val Gln Glu Leu Leu Pro Ile Asn Leu Tyr Gln Met Thr    180

481 GGA TTT TTA GCC CAA GAG GAG GAG AGA ATT ACG GCT ATA GCG GAC CAC CGG GGC AGA GCC AGG
    Gly Phe Leu Ala Gln Glu Glu Glu Arg Ile Thr Ala Ile Ala Asp His Arg Gly Ala Arg    200

541 CCG GAA ATG TGG GAG GAG AGA ATT ACG GCT ATA GCT TGG ACG TAT GCT TAT GCG GAC CTG CAG CTG GAG ATG GGC TAT GGT GTG AAC
    Pro Glu Met Trp Glu Glu Arg Ile Thr Ala Ile Trp Thr Tyr Ala Gln Ala Asp Leu Glu Met Gly Tyr Gly Val Asn    220

601 GAT GAA GCT GAA ATG GAG GAG TAT TTG TAT CTG CAG GAT CTG GAG ATG GGT GTG AAC
    Asp Glu Ala Glu Met Glu Lys Tyr Leu Lys Ala Gln Ala Asp Leu Glu Met Gly Val Asn    220

661 TAC TTT ACA ATC CGG AAT AAA AAG GGC ACA GAG TTG CTG CTT GGA GTG GAT GCT CTT GGG
    Tyr Phe Thr Ile Arg Asn Lys Lys Gly Thr Glu Leu Leu Leu Gly Val Asp Ala Leu Gly    240
```

FIG. 3A

```
721  CTT CAT ATC TAT GAC CCT GAG AAC AGG CTG ACC CCC AAG ATC TCC TTC CCA TGG AAT GAA
     Leu His Ile Tyr Asp Pro Glu Asn Arg Leu Thr Pro Lys Ile Ser Phe Pro Trp Asn Glu  260

781  ATC CGA AAC ATC TCC TAC AGC GAC AAG TTT ACT ATT AAA CTG GAT CCA CTG AAG AAA ATT
     Ile Arg Asn Ile Ser Tyr Ser Asp Lys Phe Thr Ile Lys Leu Asp Pro Leu Lys Lys Ile  280

841  GAT GTC TTC AAA TTT AAC TCA AAG CTT CGT GTT AAT AAG CTG ATT CTT CAG CTA TGT
     Asp Val Phe Lys Phe Asn Ser Lys Leu Arg Val Asn Lys Leu Ile Leu Gln Leu Cys      300

901  ATT GGG AAC CAT GAC CTA TTT ATG AGG CGA CGG AAA GCT GAC TCT TTA GAA GTT CAG CAG
     Ile Gly Asn His Asp Leu Phe Met Arg Arg Arg Lys Ala Asp Ser Leu Glu Val Gln Gln  320

961  ATG AAA GCC CAG GCC ATG GAA GAG AAG CAG ATG GAA AGG CAG CGG CTG GCT
     Met Lys Ala Gln Ala Arg Glu Glu Lys Gln Met Glu Arg Gln Arg Leu Ala              340

1021 CGA GAG AAG CAG ATG CGG GAG ATG GAG GAT ACA CGT GAG CGT ACA GAG AGG CTC
     Arg Glu Lys Gln Met Arg Glu Met Glu Asp Thr Arg Glu Arg Thr Glu Arg Leu          360

1081 CTG CAG GAT CTG AAA GAA GAA GCA ACG GCC ATG CTG CGC ATG TCT GAG GAG ACA
     Leu Gln Met Lys Asp Leu Ala Thr Ala Met Leu Arg Met Ser Glu Glu Thr              380

1141 GCT GAT CTG TTG GCT GCT GAA AAG GCT CAG AAG GAG CAA GAG ATC CGG AAG CTT TTG GCA CAA
     Ala Asp Leu Leu Ala Ala Glu Lys Ala Gln Lys Glu Gln Glu Ile Arg Lys Leu Leu Ala Gln  400

1201 AAG CGC GCT GAG GAG ATG GAG CAG CAG ATG GAG CAG CTG GTG CTG GCA TTG AAC ATG
     Lys Arg Ala Glu Glu Met Glu Gln Gln Met Glu Gln Leu Val Leu Ala Leu Asn Met      420

1261 GAG GAG AAG CGC CTG ATG AAG GAG CAG GAG CGG GCT GAA GTG CTG GCA TTG AAC ATG
     Glu Glu Lys Arg Leu Met Lys Glu Gln Glu Arg Ala Glu Val Leu Ala Leu Asn Met      440

1321 GCT GAG GAG TCA GAG AGG AGG CGA GAG GCT GAT CAG TTA AAG CAA GAC TTG CAA GAA
     Ala Glu Glu Ser Glu Arg Arg Arg Glu Ala Asp Gln Leu Lys Gln Asp Leu Gln Glu      460

1381 GCC AGA GAA GCA GAG CGA AGA GCC AAG CTC TTA GAA ATC GCC ACC AAG CCC ACC
     Ala Arg Glu Ala Glu Arg Arg Ala Lys Leu Leu Glu Ile Ala Thr Lys Pro Thr          480
```

*FIG. 3B*

```
1441  TAT CCA CCC ATG AAC CCA ATT CCA CCA CTG CCT CCT GAC ATA CCG AGC TTC GAC ATT
      Tyr Pro Pro Met Asn Pro Ile Pro Pro Leu Pro Pro Asp Ile Pro Ser Phe Asp Ile   500

1501  ATT GCT GAC AGC TTG TCA TTC GAC TTC AAG GAC ATG GAT ACG AAG CGA CTT TCC ATG GAG
      Ile Ala Asp Ser Leu Ser Phe Asp Phe Lys Asp Met Asp Thr Lys Arg Leu Ser Met Glu   520

1561  ATA GAG AAA GAA AAA GTG TAC ATG GAG AAG AGC CTG AAG AGC CAC AAG GAG CAG CTC AAC
      Ile Glu Lys Glu Lys Val Tyr Met Glu Lys Ser Leu Lys Ser His Lys Glu Gln Leu Asn   540

1621  GAG CTC AAG ACG ATC GAG GCC TTG AAA CTC AAA CTC AAA GAG CGG GAG ACG GCC TTG GAC GTC
      Glu Leu Lys Thr Ile Glu Ala Leu Lys Leu Lys Leu Lys Glu Arg Glu Thr Ala Leu Asp Val   560

1681  CTA CAC AGC GAG AGC TCA GAC AGA GGC GGC AGC AAG CAT AAT ACC ATT AAA AAG
      Leu His Ser Glu Ser Ser Asp Arg Gly Gly Ser Ser Lys His Asn Thr Ile Lys Lys   580

1741  GTA CCT GAA ATG TGA GCT CAC TCT GCA GAG CGC CAA GTC CCG AGT GGC CTT TGA AGA
      Val Pro Glu Met ***  584

1801  ACT CTA Gcaggtgacc-3'
```

FIG. 3C

```
         5        10        15        20        25        30        35        40        45        50        55        60
                  *                   *                   *                   *                   *                   *
ACGGCAGCCG TCAGGGACCT GCCCCCAACT CCCCTTTCCG CTCAGGCAGG GTCCTCGCGG 65        70        75        80        85        90        95       100       105       110       115       120
                  *                   *                   *                   *                   *                   *
CCCATGCTGG CCGCTGGGGA CCCGCGCAGC CCAGACCGTT CCCGGGCCGG CCAGCCGGCA 125       130       135       140       145       150       155       160       165       170       175       180
                  *                   *                   *                   *                   *                   *
CCATGGTGGC CCTGAGGCCT GTGCAGCAAC TCCAGGGGGG CTAAAGGGCT CAGAGTGCAG 185       190       195       200       205       210       215       220       225       230       235
                  *                   *                   *                   *                   *
GCCGTGGGGC GCGAGGGTCC CGGGCCTGAG CCCCGCGCC  ATG GCC GGG GCC ATC GCT
                                            Met Ala Gly Ala Ile Ala>
                                                TRANSLATION OF N   >

240       245       250       255       260       265       270       275       280       285
             *                   *                   *                   *                   *
TCC CGC ATG AGC TTC AGC TCT CTC AAG AGG AAG CAA CCC AAG ACG TTC
Ser Arg Met Ser Phe Ser Ser Leu Lys Arg Lys Gln Pro Lys Thr Phe>
 a   a   a   a   TRANSLATION OF NF2 II  [A]   a   a   a   a    >

290       295       300       305       310       315       320       325       330
                  *                   *                   *                   *                   *
ACC GTG AGG ATC GTC ACC ATG GAC GCC GAG ATG GAG TTC AAT TGC GAG
Thr Val Arg Ile Val Thr Met Asp Ala Glu Met Glu Phe Asn Cys Glu>
 a   a   a   a   TRANSLATION OF NF2 II  [A]   a   a   a   a    >

ATG AAG TGG AAA GGG AAG GAC CTC TTT GAT TTG GTG TGC CGG ACT CTG
Met Lys Trp Lys Gly Lys Asp Leu Phe Asp Leu Val Cys Arg Thr Leu>
 a   a   a   a   TRANSLATION OF NF2 II  [A]   a   a   a   a    >

385       390       395       400       405       410       415       420       425
             *                   *                   *                   *
GGG CTC CGA GAA ACC TGG TTC TTT GGA CTG CAG TAC ACA ATC AAG GAC
Gly Leu Arg Glu Thr Trp Phe Phe Gly Leu Gln Tyr Thr Ile Lys Asp>
 a   a   a   a   TRANSLATION OF NF2 II  [A]   a   a   a   a    >

430       435       440       445       450       455       460       465       470       475
 *                   *                   *                   *                   *
ACA GTG GCC TGG CTC AAA ATG GAC AAG AAG GTA CTG GAT CAT GAT GTT
Thr Val Ala Trp Leu Lys Met Asp Lys Lys Val Leu Asp His Asp Val>
 a   a   a   a   TRANSLATION OF NF2 II  [A]   a   a   a   a    >

480       485       490       495       500       505       510       515       520       525
             *                   *                   *                   *                   *
TCA AAG GAA GAA CCA GTC ACC TTT CAC TTC TTG GCC AAA TTT TAT CCT
Ser Lys Glu Glu Pro Val Thr Phe His Phe Leu Ala Lys Phe Tyr Pro>
 a   a   a   a   TRANSLATION OF NF2 II  [A]   a   a   a   a    >

530       535       540       545       550       555       560       565       570
                  *                   *                   *                   *                   *
GAG AAT GCT GAA GAG GAG CTG GTT CAG GAG ATC ACA CAA CAT TTA TTC>
Glu Asn Ala Glu Glu Glu Leu Val Gln Glu Ile Thr Gln His Leu Phe>
 a   a   a   a   TRANSLATION OF NF2 II  [A]   a   a   a   a    >

575       580       585       590       595       600       605       610       615       620
             *                   *                   *                   *                   *
TTC TTA CAG GTA AAG AAG CAG ATT TTA GAT GAA AAG ATC TAC TGC CCT
Phe Leu Gln Val Lys Lys Gln Ile Leu Asp Glu Lys Ile Tyr Cys Pro>
 a   a   a   a   TRANSLATION OF NF2 II  [A]   a   a   a   a    >
```

FIG. 7A

```
       625      630      635      640      645      650      655      660      665
                 *                          *                          *                          *
CCT GAG GCT TCT GTG CTC CTG GCT TCT TAC GCC GTC CAG GCC AAG TAT
Pro Glu Ala Ser Val Leu Leu Ala Ser Tyr Ala Val Gln Ala Lys Tyr>
     a   a   a   a   TRANSLATION OF NF2 II  [A]   a   a   a   a   >

670      675      680      685      690      695      700      705      710      715
    *                          *                          *                          *
GGT GAC TAC GAC CCC AGT GTT CAC AAG CGG GGA TTT TTG GCC CAA GAG
Gly Asp Tyr Asp Pro Ser Val His Lys Arg Gly Phe Leu Ala Gln Glu>
     a   a   a   a   TRANSLATION OF NF2 II  [A]   a   a   a   a   >

720      725      730      735      740      745      750      755      760      765
                 *                          *                          *                          *
GAA TTG CTT CCA AAA AGG GTA ATA AAT CTG TAT CAG ATG ACT CCG GAA
Glu Leu Leu Pro Lys Arg Val Ile Asn Leu Tyr Gln Met Thr Pro Glu>
     a   a   a   a   TRANSLATION OF NF2 II  [A]   a   a   a   a   >

770      775      780      785      790      795      800      805      810
                 *                          *                          *                          *
ATG TGG GAG GAG AGA ATT ACT GCT TGG TAC GCA GAG CAC CGA GGC CGA
Met Trp Glu Glu Arg Ile Thr Ala Trp Tyr Ala Glu His Arg Gly Arg>
     a   a   a   a   TRANSLATION OF NF2 II  [A]   a   a   a   a   >

815      820      825      830      835      840      845      850      855      860
                 *                          *                          *                          *
GCC AGG GAT GAA GCT GAA ATG GAA TAT CTG AAG ATA GCT CAG GAC CTG
Ala Arg Asp Glu Ala Glu Met Glu Tyr Leu Lys Ile Ala Gln Asp Leu>
     a   a   a   a.  TRANSLATION OF NF2 II  [A]   a   a   a   a   >

865      870      875      880      885      890      895      900      905
GAG ATG TAC GGT GTG AAC TAC TTT GCA ATC CGG AAT AAA AAG GGC ACA
Glu Met Tyr Gly Val Asn Tyr Phe Ala Ile Arg Asn Lys Lys Gly Thr>
     a   a   a   a   TRANSLATION OF NF2 II  [A]   a   a   a   a   >

910      915      920      925      930      935      940      945      950      955
 *                          *                          *                          *
GAG CTG CTG CTT GGA GTG GAT GCC CTG GGG CTT CAC ATT TAT GAC CCT
Glu Leu Leu Leu Gly Val Asp Ala Leu Gly Leu His Ile Tyr Asp Pro>
     a   a   a   a   TRANSLATION OF NF2 II  [A]   a   a   a   a   >

960      965      970      975      980      985      990      995     1000     1005
    *                          *                          *                          *
GAG AAC AGA CTG ACC CCC AAG ATC TCC TTC CCG TGG AAT GAA ATC CGA
Glu Asn Arg Leu Thr Pro Lys Ile Ser Phe Pro Trp Asn Glu Ile Arg>
     a   a   a   a   TRANSLATION OF NF2 II  [A]   a   a   a   a   >

1010     1015     1020     1025     1030     1035     1040     1045     1050
            *                          *                          *                          *
AAC ATC TCG TAC AGT GAC AAG GAG TTT ACT ATT AAA CCA CTG GAT AAG
Asn Ile Ser Tyr Ser Asp Lys Glu Phe Thr Ile Lys Pro Leu Asp Lys>
     a   a   a   a   TRANSLATION OF NF2 II  [A]   a   a   a   a   >

1055    1060    1065    1070    1075    1080    1085    1090    1095    1100
                 *                          *                          *                          *
AAA ATT GAT GTC TTC AAG TTT AAC TCC TCA AAG CTT CGT GTT AAT AAG
Lys Ile Asp Val Phe Lys Phe Asn Ser Ser Lys Leu Arg Val Asn Lys>
     a   a   a   a   TRANSLATION OF NF2 II  [A]   a   a   a   a   >

1105    1110    1115    1120    1125    1130    1135    1140    1145
                 *                          *                          *
CTG ATT CTC CAG CTA TGT ATC GGG AAC CAT GAT CTA TTT ATG AGG AGA
Leu Ile Leu Gln Leu Cys Ile Gly Asn His Asp Leu Phe Met Arg Arg>
     a   a   a   a   TRANSLATION OF NF2 II  [A]   a   a   a   a   >
```

FIG.7B

```
      1150   1155   1160   1165   1170   1175   1180   1185   1190   1195
        *             *             *             *             *
   AGG AAA GCC GAT TCT TTG GAA GTT CAG CAG ATG AAA GCC CAG GCC AGG
   Arg Lys Ala Asp Ser Leu Glu Val Gln Gln Met Lys Ala Gln Ala Arg>
        a   a   a   a   TRANSLATION OF NF2 II  [A]  a   a   a   a   >

1200   1205   1210   1215   1220   1225   1230   1235   1240   1245
        *             *             *             *             *
   GAG GAG AAG GCT AGA AAG CAG ATG GAG CGG CAG CGC CTC GCT CGA GAG
   Glu Glu Lys Ala Arg Lys Gln Met Glu Arg Gln Arg Leu Ala Arg Glu>
        a   a   a   a   TRANSLATION OF NF2 II  [A]  a   a   a   a   >

1250   1255   1260   1265   1270   1275   1280   1285   1290
           *             *             *             *             *
   AAG CAG ATG AGG GAG GAG GCT GAA CGC ACG AGG GAT GAG TTG GAG AGG
   Lys Gln Met Arg Glu Glu Ala Glu Arg Thr Arg Asp Glu Leu Glu Arg>
        a   a   a   a   TRANSLATION OF NF2 II  [A]  a   a   a   a   >

1295   1300   1305   1310   1315   1320   1325   1330   1335   1340
     *             *             *             *             *
   AGG CTG CTG CAG ATG AAA GAA GAA GCA ACA ATG GCC AAC GAA GCA CTG
   Arg Leu Leu Gln Met Lys Glu Glu Ala Thr Met Ala Asn Glu Ala Leu>
        a   a   a   a   TRANSLATION OF NF2 II  [A]  a   a   a   a   >

1345   1350   1355 1360    1365   1370   1375   1380   1385
        *             *             *             *
   ATG CGG TCT GAG GAG ACA GCT GAC CTG TTG GCT GAA AAG GCC CAG ATC
   Met Arg Ser Glu Glu Thr Ala Asp Leu Leu Ala Glu Lys Ala Gln Ile>
        a   a   a   a   TRANSLATION OF NF2 II  [A]  a   a   a   a   >

1390   1395   1400   1405   1410   1415   1420   1425   1430   1435
     *             *             *             *             *
   ACC GAG GAG GAG GCA AAA CTT CTG GCC CAG AAG GCC GCA GAG GCT GAG
   Thr Glu Glu Glu Ala Lys Leu Leu Ala Gln Lys Ala Ala Glu Ala Glu>
        a   a   a   a   TRANSLATION OF NF2 II  [A]  a   a   a   a   >

1440   1445   1450   1455   1460   1465   1470   1475   1480   1485
     *             *             *             *             *
   CAG GAA ATG CAG CGC ATC AAG GCC ACA GCG ATT CGC ACG GAG GAG GAG
   Gln Glu Met Gln Arg Ile Lys Ala Thr Ala Ile Arg Thr Glu Glu Glu>
        a   a   a   a   TRANSLATION OF NF2 II  [A]  a   a   a   a   >

1490   1495   1500   1505   1510   1515   1520   1525   1530
           *             *             *             *             *
   AAG CGC CTG ATG GAG CAG AAG GTG CTG GAA GCC GAG GTG CTG GCA CTG
   Lys Arg Leu Met Glu Gln Lys Val Leu Glu Ala Glu Val Leu Ala Leu>
        a   a   a   a   TRANSLATION OF NF2 II  [A]  a   a   a   a   >

1535   1540   1545   1550   1555   1560   1565   1570   1575   1580
        *             *             *             *             *
   AAG ATG GCT GAG GAG TCA GAG AGG AGG GCC AAA GAG GCA GAT CAG CTG
   Lys Met Ala Glu Glu Ser Glu Arg Arg Ala Lys Glu Ala Asp Gln Leu>
        a   a   a   a   TRANSLATION OF NF2 II  [A]  a   a   a   a   >

1585   1590   1595   1600   1605   1610   1615   1620   1625
           *             *             *             *
   AAG CAG GAC CTG CAG GAA GCA CGC GAG GCG GAG CGA AGA GCC AAG CAG
   Lys Gln Asp Leu Gln Glu Ala Arg Glu Ala Glu Arg Arg Ala Lys Gln>
        a   a   a   a   TRANSLATION OF NF2 II  [A]  a   a   a   a   >

1630   1635   1640   1645   1650   1655   1660   1665   1670   1675
     *             *             *             *             *
   AAG CTC CTG GAG ATT GCC ACC AAG CCC ACG TAC CCG CCC ATG AAC CCA
   Lys Leu Leu Glu Ile Ala Thr Lys Pro Thr Tyr Pro Pro Met Asn Pro>
        a   a   a   a   TRANSLATION OF NF2 II  [A]  a   a   a   a   >
```

FIG.7C

```
     1680      1685      1690      1695      1700      1705      1710      1715      1720      1725
       *                   *                   *                   *                   *
     ATT  CCA  GCA  CCG  TTG  CCT  CCT  GAC  ATA  CCA  AGC  TTC  AAC  CTC  ATT  GGT
     Ile  Pro  Ala  Pro  Leu  Pro  Pro  Asp  Ile  Pro  Ser  Phe  Asn  Leu  Ile  Gly>
       a    a    a    a    TRANSLATION OF NF2 II   [A]    a    a    a    a    >

1730      1735      1740      1745      1750      1755      1760      1765      1770
           *                   *                   *                   *                   *
         GAC  AGC  CTG  TCT  TTC  GAC  TTC  AAA  GAT  ACT  GAC  ATG  AAG  CGG  CTT  TCC
         Asp  Ser  Leu  Ser  Phe  Asp  Phe  Lys  Asp  Thr  Asp  Met  Lys  Arg  Leu  Ser>
           a    a    a    a    TRANSLATION OF NF2 II   [A]    a    a    a    a    >

1775      1780    1785      1790      1795    1800      1805      1810    1815      1820
       *                   *                   *                   *                   *
     ATG  GAG  ATA  GAG  AAA  GAA  AAA  GTG  GAA  TAC  ATG  GAA  AAG  AGC  AAG  CAT
•    Met  Glu  Ile  Glu  Lys  Glu  Lys  Val  Glu  Tyr  Met  Glu  Lys  Ser  Lys  His>
       a    a    a    a    TRANSLATION OF NF2 II   [A]    a    a    a    a    >

1825      1830      1835      1840      1845      1850      1855      1860      1865
     *                   *                   *                   *
   CTG  CAG  GAG  CAG  CTC  AAT  GAA  CTC  AAG  ACA  GAA  ATC  GAG  GCC  TTG  AAA
   Leu  Gln  Glu  Gln  Leu  Asn  Glu  Leu  Lys  Thr  Glu  Ile  Glu  Ala  Leu  Lys>
     a    a    a    a    TRANSLATION OF NF2 II   [A]    a    a    a    a    >

1870    1875      1880      1885    1890      1895      1900    1905      1910      1915
     *                   *                   *                   *                   *
   CTG  AAA  GAG  AGG  GAG  ACA  GCT  CTG  GAT  ATT  CTG  CAC  AAT  GAG  AAC  TCC
   Leu  Lys  Glu  Arg  Glu  Thr  Ala  Leu  Asp  Ile  Leu  His  Asn  Glu  Asn  Ser>
     a    a    a    a    TRANSLATION OF NF2 II   [A]    a    a    a    a    >

1920      1925      1930      1935      1940      1945  1950      1955      1960      1965
       *                   *                   *                   *                   *
     GAC  AGG  GGT  GGC  AGC  AGC  AAG  CAC  AAT  ACC  ATT  AAA  AAG  CCT  CAA  GCC
     Asp  Arg  Gly  Gly  Ser  Ser  Lys  His  Asn  Thr  Ile  Lys  Lys  Pro  Gln  Ala>
       a    a    a    a    TRANSLATION OF NF2 II   [A]    a    a    a    a    >

1970      1975      1980      1985      1990  1995  2000      2005 2010      2015 2020
           *                   *                   *                   *                   *
         CAA  GGC  AGA  AGA  CCT  ATC  TGC  ATT  TGA  GCCCTCAA ACTCACCTTG  CAGAGCGCCA
         Gln  Gly  Arg  Arg  Pro  Ile  Cys  Ile  ***>
              TRANSLATION OF NF2 II   [A]    a    >

2025 2030    2035 2040    2045 2050    2055 2060    2065 2070    2075 2080
           *             *             *             *             *             *
       AGTCCCGAGT   GGCCTTCTTT   GAAGAGCTCT   AGCAGGTGAC   CCAGCCACCC   CAGGACCTGC 2085 2090    2095 2100    2105 2110    2115 2120    2125 2130    2135 2140
           *             *             *             *             *             *
```

FIG. 7D

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:

( A ) LENGTH: 1817 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: murine ( x i ) SEQUENCE DESCRIPTION: SEQ ID NO:1:

| GCGCCCGGTA | CCTCGCGATG | GCCGGAGCCA | TCGCTTCTCG | CATGAGCTTC | AGCTCACTCA | 60 |
| AGAGGAAGCA | GCCCAAGACA | TTCACGGTGC | GGATCGTCAC | CATGGACGCC | GAGATGGAGT | 120 |
| TCAACTGCGA | GATGAAATGG | AAGGGGAAGG | ACCTGTTTGA | TTTGGTGTGC | CGGACACTGG | 180 |
| GGCTTCGGGA | AACCTGGTTC | TTTGGACTGC | AGTATACAAT | CAAGGACACG | GTGGCCTGGC | 240 |
| TCAAAATGGA | CAAGAAGGTG | TTGGATCATG | ATGTTTCGAA | GGAAGAACCA | GTTACCTTTC | 300 |
| ACTTCCTGGC | CAAATTTTAT | CCTGAAAATG | CTGAGGAGGA | GCTAGTTCAA | GAGATCACGC | 360 |
| AACACTTATT | TTTCTTACAG | GTGAAGAAGC | AGATTTTGGA | TGAAAAGGTC | TACTGCCCTC | 420 |
| CCGAGGCGTC | CGTGCTCTTG | GCGTCATATG | CTGTCCAGGC | CAAGTATGGC | GACTATGACC | 480 |
| CCTCTGTGCA | CAAGCGGGGA | TTTTTAGCCC | AAGAGGAATT | GCTCCCGAAA | AGGGTGATAA | 540 |
| ATCTCTATCA | GATGACTCCG | GAAATGTGGG | AGGAGAGAAT | TACGGCTTGG | TATGCGGAGC | 600 |
| ACCGGGGCAG | AGCCAGGGAT | GAAGCTGAAA | TGGAGTATTT | GAAGATAGCT | CAGGACCTGG | 660 |
| AGATGTATGG | TGTGAACTAC | TTTACAATCC | GGAATAAAAA | GGGCACAGAG | TTGCTGCTTG | 720 |
| GAGTGGATGC | TCTTGGGCTT | CATATCTATG | ACCCTGAGAA | CAGGCTGACC | CCCAAGATCT | 780 |
| CCTTCCCATG | GAATGAAATC | CGAAACATCT | CCTACAGCGA | CAAGGAGTTT | ACTATTAAAC | 840 |
| CACTGGATAA | GAAAATTGAT | GTCTTCAAAT | TTAACTCCTC | AAAGCTTCGT | GTTAATAAGC | 900 |
| TGATTCTTCA | GCTATGTATT | GGGAACCATG | ACCTATTTAT | GAGGCGACGG | AAAGCTGACT | 960 |
| CTTTAGAAGT | TCAGCAGATG | AAAGCCCAGG | CCAGGGAAGA | GAAGGCTAGA | AAGCAGATGG | 1020 |
| AAAGGCAGCG | GCTGGCTCGA | GAGAAGCAGA | TGCGGGAGGA | GGCCGAGCGT | ACAAGAGATG | 1080 |
| AGTTAGAGAG | GAGGCTCCTG | CAGATGAAAG | AAGAAGCAAC | GATGGCCAAT | GAAGCTCTGA | 1140 |
| TGCGCTCTGA | GGAGACAGCT | GATCTGTTGG | CTGAAAAGGC | TCAGATCACA | GAGGAGGAGG | 1200 |
| CCAAGCTTTT | GGCACAAAAG | GCTGCAGAGG | CTGAGCAAGA | GATGCAGCGA | ATCAAGGCCA | 1260 |
| CGGCCATTCG | GACAGAGGAG | GAGAAGCGCC | TGATGGAGCA | GAAGGTGCTG | GAGGCTGAAG | 1320 |
| TGCTGGCATT | GAACATGGCT | GAGGAGTCAG | AGAGGAGGGC | CAAGGAGGCT | GATCAGTTAA | 1380 |
| AGCAAGACTT | GCAAGAAGCC | AGAGAAGCAG | AGCGAAGAGC | CAAGCAGAAG | CTCTTAGAAA | 1440 |
| TCGCCACCAA | GCCCACCTAT | CCACCCATGA | ACCCAATTCC | ACCACCACTG | CCTCCTGACA | 1500 |
| TACCGAGCTT | CGACATTATT | GCTGACAGCT | TGTCATTCGA | CTTCAAGGAT | ACGGACATGA | 1560 |
| AGCGACTTTC | CATGGAGATA | GAGAAAGAAA | AAGTGGAGTA | CATGGAGAAG | AGCAAGCACC | 1620 |
| TGCAGGAGCA | GCTCAACGAG | CTCAAGACGG | AGATCGAGGC | CTTGAAACTC | AAAGAGCGGG | 1680 |
| AGACGGCCTT | GGACGTCCTA | CACAGCGAGA | GCTCAGACAG | AGGCGGCCCC | AGCAGCAAGC | 1740 |
| ATAATACCAT | TAAAAAGCTC | ACTCTGCAGA | GCGCCAAGTC | CCGAGTGGCC | TTCTTTGAAG | 1800 |
| AACTCTAGCA | GGTGACC | | | | | 1817 |

( 2 ) INFORMATION FOR SEQ ID NO:2:

(i) SEQUENCE CHARACTERISTICS:
    (A) LENGTH: 596 amino acids
    (B) TYPE: amino acid
    (D) TOPOLOGY: linear (ii) MOLECULE TYPE: protein (v) FRAGMENT TYPE: N-terminal (vi) ORIGINAL SOURCE:
    (A) ORGANISM: murine (xi) SEQUENCE DESCRIPTION: SEQ ID NO:2:

```
Met Ala Gly Ala Ile Ala Ser Arg Met Ser Phe Ser Ser Leu Lys Arg
 1               5                  10                  15

Lys Gln Pro Lys Thr Phe Thr Val Arg Ile Val Thr Met Asp Ala Glu
            20                  25                  30

Met Glu Phe Asn Cys Glu Met Lys Trp Lys Gly Lys Asp Leu Phe Asp
        35                  40                  45

Leu Val Cys Arg Thr Leu Gly Leu Arg Asp Thr Trp Phe Phe Gly Leu
    50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Glu Leu Val Gln Glu
               100                 105                 110

Ile Thr Gln His Leu Phe Phe Leu Gln Val Lys Lys Gln Ile Leu Asp
           115                 120                 125

Glu Lys Val Tyr Cys Pro Pro Glu Ala Ser Val Leu Leu Ala Ser Tyr
        130                 135                 140

Ala Val Gln Ala Lys Tyr Gly Asp Tyr Asp Pro Ser Val His Lys Arg
145                 150                 155                 160

Gly Phe Leu Ala Gln Glu Glu Leu Leu Pro Lys Arg Val Ile Asn Leu
                165                 170                 175

Tyr Gln Met Thr Pro Glu Met Trp Glu Glu Arg Ile Thr Ala Trp Tyr
               180                 185                 190

Ala Glu His Arg Gly Arg Ala Arg Asp Glu Ala Glu Met Glu Tyr Leu
           195                 200                 205

Lys Ile Ala Gln Asp Leu Glu Met Tyr Gly Val Asn Tyr Phe Thr Ile
        210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                245                 250                 255

Pro Trp Asn Glu Ile Arg Asn Ile Ser Tyr Ser Asp Lys Glu Phe Thr
               260                 265                 270

Ile Lys Pro Leu Asp Lys Lys Ile Asp Val Phe Lys Phe Asp Ser Ser
           275                 280                 285

Lys Leu Arg Val Asn Lys Leu Ile Leu Gln Leu Cys Ile Gly Asn His
        290                 295                 300

Asp Leu Phe Met Arg Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
                325                 330                 335

Gln Arg Leu Ala Arg Glu Lys Gln Met Arg Glu Glu Ala Glu Arg Thr
               340                 345                 350
```

```
Arg  Asp  Glu  Leu  Glu  Arg  Arg  Leu  Leu  Gln  Met  Lys  Glu  Glu  Ala  Thr
          355                      360                     365

Met  Ala  Asn  Glu  Ala  Leu  Met  Arg  Ser  Glu  Glu  Thr  Ala  Asp  Leu  Leu
     370                      375                     380

Ala  Glu  Lys  Ala  Gln  Ile  Thr  Glu  Glu  Glu  Ala  Lys  Leu  Leu  Ala  Gln
385                      390                     395                          400

Lys  Ala  Ala  Glu  Ala  Glu  Gln  Glu  Met  Gln  Arg  Ile  Lys  Ala  Thr  Ala
                    405                     410                     415

Ile  Arg  Thr  Glu  Glu  Glu  Lys  Arg  Leu  Met  Glu  Gln  Lys  Val  Leu  Glu
               420                      425                     430

Ala  Glu  Val  Leu  Ala  Leu  Asn  Met  Ala  Glu  Glu  Ser  Glu  Arg  Arg  Ala
          435                      440                     445

Lys  Glu  Ala  Asp  Gln  Leu  Lys  Gln  Asp  Leu  Gln  Glu  Ala  Arg  Glu  Ala
     450                      455                     460

Glu  Arg  Arg  Ala  Lys  Gln  Lys  Leu  Leu  Glu  Ile  Ala  Thr  Lys  Pro  Thr
465                      470                     475                          480

Tyr  Pro  Pro  Met  Asn  Pro  Ile  Pro  Pro  Leu  Pro  Pro  Asp  Ile  Pro
                    485                     490                     495

Ser  Phe  Asp  Ile  Ile  Ala  Asp  Ser  Leu  Ser  Phe  Asp  Phe  Lys  Asp  Thr
          500                      505                     510

Asp  Met  Lys  Arg  Leu  Ser  Met  Glu  Ile  Glu  Lys  Glu  Lys  Val  Glu  Tyr
               515                      520                     525

Met  Glu  Lys  Ser  Lys  His  Leu  Gln  Glu  Gln  Leu  Asn  Glu  Leu  Lys  Thr
     530                      535                     540

Glu  Ile  Glu  Ala  Leu  Lys  Leu  Lys  Glu  Arg  Glu  Thr  Ala  Leu  Asp  Val
545                      550                     555                          560

Leu  His  Ser  Glu  Ser  Ser  Asp  Arg  Gly  Gly  Pro  Ser  Ser  Lys  His  Asp
                    565                     570                     575

Thr  Ile  Lys  Lys  Leu  Thr  Leu  Gln  Ser  Ala  Lys  Ser  Arg  Val  Ala  Phe
               580                      585                     590

Phe  Glu  Glu  Leu
          595
```

( 2 ) INFORMATION FOR SEQ ID NO:3:

( i ) SEQUENCE CHARACTERISTICS:
        ( A ) LENGTH: 596 amino acids
        ( B ) TYPE: amino acid
        ( D ) TOPOLOGY: linear ( i i ) MOLECULE TYPE: protein ( v ) FRAGMENT TYPE: N-terminal ( v i ) ORIGINAL SOURCE:
        ( A ) ORGANISM: Homo sapien ( x i ) SEQUENCE DESCRIPTION: SEQ ID NO:3:

```
Met  Ala  Gly  Ala  Ile  Ala  Ser  Arg  Met  Ser  Phe  Ser  Ser  Leu  Lys  Arg
1                        5                      10                          15

Lys  Gln  Pro  Lys  Thr  Phe  Thr  Val  Arg  Ile  Val  Thr  Met  Asp  Ala  Glu
               20                      25                      30

Met  Glu  Phe  Asn  Cys  Glu  Met  Lys  Trp  Lys  Gly  Lys  Asp  Leu  Phe  Asp
          35                      40                      45

Leu  Val  Cys  Arg  Thr  Leu  Gly  Leu  Arg  Glu  Thr  Trp  Phe  Phe  Gly  Leu
     50                      55                      60

Gln  Tyr  Thr  Ile  Lys  Asp  Thr  Val  Ala  Trp  Leu  Lys  Met  Asp  Lys  Lys
65                       70                      75                          80
```

```
Val Leu Asp His Asp Val Ser Lys Glu Glu Pro Val Thr Phe His Phe
             85                  90                      95

Leu Ala Lys Phe Tyr Pro Glu Asn Ala Glu Glu Leu Val Gln Glu
            100             105             110

Ile Thr Gln His Leu Phe Phe Leu Gln Val Lys Lys Gln Ile Leu Asp
            115             120             125

Glu Lys Ile Tyr Cys Pro Pro Glu Ala Ser Val Leu Leu Ala Ser Tyr
    130             135                 140

Ala Val Gln Ala Lys Tyr Gly Asp Tyr Asp Pro Ser Val His Lys Arg
145             150             155                         160

Gly Phe Leu Ala Gln Glu Leu Leu Pro Lys Arg Val Ile Asn Leu
                165             170                 175

Tyr Gln Met Thr Pro Glu Met Trp Glu Arg Ile Thr Ala Trp Tyr
            180             185             190

Ala Glu His Arg Gly Arg Ala Arg Asp Glu Ala Glu Met Glu Tyr Leu
        195             200             205

Lys Ile Ala Gln Asp Leu Glu Met Tyr Gly Val Asn Tyr Phe Ala Ile
    210             215             220

Arg Asn Lys Lys Gly Thr Glu Leu Leu Leu Gly Val Asp Ala Leu Gly
225             230             235                         240

Leu His Ile Tyr Asp Pro Glu Asn Arg Leu Thr Pro Lys Ile Ser Phe
                245             250             255

Pro Trp Asn Glu Ile Arg Asn Ile Ser Tyr Ser Asp Lys Glu Phe Thr
            260             265             270

Ile Lys Pro Leu Asp Lys Lys Ile Asp Val Phe Lys Phe Asn Ser Ser
            275             280             285

Lys Leu Arg Val Asn Lys Leu Ile Leu Gln Leu Cys Ile Gly Asn His
            290             295             300

Asp Leu Phe Met Arg Arg Arg Lys Ala Asp Ser Leu Glu Val Gln Gln
305             310             315                         320

Met Lys Ala Gln Ala Arg Glu Glu Lys Ala Arg Lys Gln Met Glu Arg
                325             330             335

Gln Arg Leu Ala Arg Glu Lys Gln Met Arg Glu Glu Ala Glu Arg Thr
            340             345             350

Arg Asp Glu Leu Glu Arg Arg Leu Leu Gln Met Lys Glu Glu Ala Thr
            355             360             365

Met Ala Asn Glu Ala Leu Met Arg Ser Glu Glu Thr Ala Asp Leu Leu
370             375             380

Ala Glu Lys Ala Gln Ile Thr Glu Glu Glu Ala Lys Leu Leu Ala Gln
385             390             395                         400

Lys Ala Ala Glu Ala Glu Gln Glu Met Gln Arg Ile Lys Ala Thr Ala
                405             410             415

Ile Arg Thr Glu Glu Glu Lys Arg Leu Met Glu Gln Lys Val Leu Glu
            420             425             430

Ala Glu Val Leu Ala Leu Lys Met Ala Glu Glu Ser Glu Arg Arg Ala
            435             440             445

Lys Glu Ala Asp Gln Leu Lys Gln Asp Leu Gln Glu Ala Arg Glu Ala
    450             455             460

Glu Arg Arg Ala Lys Gln Lys Leu Leu Glu Ile Ala Thr Lys Pro Thr
465             470             475             480

Tyr Pro Pro Met Asn Pro Ile Pro Ala Pro Leu Pro Pro Asp Ile Pro
                485             490             495

Ser Phe Asn Leu Ile Gly Asp Ser Leu Ser Phe Asp Phe Lys Asp Thr
```

|     |     | 500 |     |     |     |     | 505 |     |     |     |     | 510 |     |     |
| --- | --- | --- | --- | --- | --- | --- | --- | --- | --- | --- | --- | --- | --- | --- |
| Asp | Met | Lys | Arg | Leu | Ser | Met | Glu | Ile | Glu | Lys | Glu | Lys | Val | Glu | Tyr |
|     |     | 515 |     |     |     |     | 520 |     |     |     |     | 525 |     |     |
| Met | Glu | Lys | Ser | Lys | His | Leu | Gln | Glu | Gln | Leu | Asn | Glu | Leu | Lys | Thr |
|     |     | 530 |     |     |     |     | 535 |     |     |     |     | 540 |     |     |
| Glu | Ile | Glu | Ala | Leu | Lys | Leu | Lys | Glu | Arg | Glu | Thr | Ala | Leu | Asp | Ile |
|     |     | 545 |     |     |     |     | 550 |     |     |     |     | 555 |     |     | 560 |
| Leu | His | Asn | Glu | Asn | Ser | Asp | Arg | Gly | Gly | Pro | Ser | Ser | Lys | His | Asn |
|     |     |     |     | 565 |     |     |     |     | 570 |     |     |     |     | 575 |     |
| Thr | Ile | Lys | Lys | Leu | Thr | Leu | Gln | Ser | Ala | Lys | Ser | Arg | Val | Ala | Phe |
|     |     |     | 580 |     |     |     |     | 585 |     |     |     |     | 590 |     |     |
| Phe | Glu | Glu | Leu |     |     |     |     |     |     |     |     |     |     |     |     |
|     |     |     | 595 |     |     |     |     |     |     |     |     |     |     |     |     |

( 2 ) INFORMATION FOR SEQ ID NO:4:

( i ) SEQUENCE CHARACTERISTICS:
( A ) LENGTH: 1862 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: murine ( x i ) SEQUENCE DESCRIPTION: SEQ ID NO:4:

```
GCGCCCGGTA CCTCGCGATG GCCGGAGCCA TCGCTTCTCG CATGAGCTTC AGCTCACTCA      60
AGAGGAAGCA GCCCAAGACA TTCACGGTGC GGATCGTCAC CATGGACGCC GAGATGGAGT     120
TCAACTGCGA GATGAAATGG AAGGGGAAGG ACCTGTTTGA TTTGGTGTGC CGGACACTGG     180
GGCTTCGGGA AACCTGGTTC TTTGGACTGC AGTATACAAT CAAGGACACG GTGGCCTGGC     240
TCAAAATGGA CAAGAAGGTG TTGGATCATG ATGTTTCGAA GGAAGAACCA GTTACCTTTC     300
ACTTCCTGGC CAAATTTTAT CCTGAAAATG CTGAGGAGGA GCTAGTTCAA GAGATCACGC     360
AACACTTATT TTTCTTACAG GTGAAGAAGC AGATTTTGGA TGAAAAGGTC TACTGCCCTC     420
CCGAGGCGTC CGTGCTCTTG GCGTCATATG CTGTCCAGGC CAAGTATGGC GACTATGACC     480
CCTCTGTGCA CAAGCGGGGA TTTTTAGCCC AAGAGGAATT GCTCCCGAAA GGGTGATAA     540
ATCTCTATCA GATGACTCCG GAAATGTGGG AGGAGAGAAT TACGGCTTGG TATGCGGAGC     600
ACCGGGGCAG AGCCAGGGAT GAAGCTGAAA TGGAGTATTT GAAGATAGCT CAGGACCTGG     660
AGATGTATGG TGTGAACTAC TTTACAATCC GGAATAAAAA GGGCACAGAG TTGCTGCTTG     720
GAGTGGATGC TCTTGGGCTT CATATCTATG ACCCTGAGAA CAGGCTGACC CCCAAGATCT     780
CCTTCCCATG GAATGAAATC CGAAACATCT CCTACAGCGA CAAGGAGTTT ACTATTAAAC     840
CACTGGATAA GAAAATTGAT GTCTTCAAAT TTAACTCCTC AAAGCTTCGT GTTAATAAGC     900
TGATTCTTCA GCTATGTATT GGGAACCATG ACCTATTTAT GAGGCGACGG AAAGCTGACT     960
CTTTAGAAGT TCAGCAGATG AAAGCCCAGG CCAGGGAAGA GAAGGCTAGA AAGCAGATGG    1020
AAAGGCAGCG GCTGGCTCGA GAGAAGCAGA TGCGGGAGGA GGCCGAGCGT ACAAGAGATG    1080
AGTTAGAGAG GAGGCTCCTG CAGATGAAAG AAGAAGCAAC GATGGCCAAT GAAGCTCTGA    1140
TGCGCTCTGA GGAGACAGCT GATCTGTTGG CTGAAAAGGC TCAGATCACA GAGGAGGAGG    1200
```

33

-continued

| | | | | | |
|---|---|---|---|---|---|
| CCAAGCTTTT | GGCACAAAAG | GCTGCAGAGG | CTGAGCAAGA | GATGCAGCGA | ATCAAGGCCA | 1260 |
| CGGCCATTCG | GACAGAGGAG | GAGAAGCGCC | TGATGGAGCA | GAAGGTGCTG | GAGGCTGAAG | 1320 |
| TGCTGGCATT | GAACATGGCT | GAGGAGTCAG | AGAGGAGGGC | CAAGGAGGCT | GATCAGTTAA | 1380 |
| AGCAAGACTT | GCAAGAAGCC | AGAGAAGCAG | AGCGAAGAGC | CAAGCAGAAG | CTCTTAGAAA | 1440 |
| TCGCCACCAA | GCCCACCTAT | CCACCCATGA | ACCCAATTCC | ACCACCACTG | CCTCCTGACA | 1500 |
| TACCGAGCTT | CGACATTATT | GCTGACAGCT | TGTCATTCGA | CTTCAAGGAT | ACGGACATGA | 1560 |
| AGCGACTTTC | CATGGAGATA | GAGAAAGAAA | AAGTGGAGTA | CATGGAGAAG | AGCAAGCACC | 1620 |
| TGCAGGAGCA | GCTCAACGAG | CTCAAGACGG | AGATCGAGGC | CTTGAAACTC | AAAGAGCGGG | 1680 |
| AGACGGCCTT | GGACGTCCTA | CACAGCGAGA | GCTCAGACAG | AGGCGGCCCC | AGCAGCAAGC | 1740 |
| ATAATACCAT | TAAAAAGCCT | CAAGCCCAAG | GCAGAAGACC | TATCTGCATT | TGAGTCCTCA | 1800 |
| AACTCACTCT | GCAGAGCGCC | AAGTCCCGAG | TGGCCTTCTT | TGAAGAACTC | TAGCAGGTGA | 1860 |
| CC | | | | | | 1862 |

(2) INFORMATION FOR SEQ ID NO:5:

(i) SEQUENCE CHARACTERISTICS:
(A) LENGTH: 591 amino acids
(B) TYPE: amino acid
(D) TOPOLOGY: linear (ii) MOLECULE TYPE: protein (v) FRAGMENT TYPE: N-terminal (vi) ORIGINAL SOURCE:
(A) ORGANISM: murine (xi) SEQUENCE DESCRIPTION: SEQ ID NO:5:

| Met | Ala | Gly | Ala | Ile | Ala | Ser | Arg | Met | Ser | Phe | Ser | Ser | Leu | Lys | Arg |
|---|---|---|---|---|---|---|---|---|---|---|---|---|---|---|---|
| 1 | | | | 5 | | | | | 10 | | | | | 15 | |
| Lys | Gln | Pro | Lys | Thr | Phe | Thr | Val | Arg | Ile | Val | Thr | Met | Asp | Ala | Glu |
| | | | 20 | | | | | 25 | | | | | 30 | | |
| Met | Glu | Phe | Asn | Cys | Glu | Met | Lys | Trp | Lys | Gly | Lys | Asp | Leu | Phe | Asp |
| | | 35 | | | | | 40 | | | | | 45 | | | |
| Leu | Val | Cys | Arg | Thr | Leu | Gly | Leu | Arg | Asp | Thr | Trp | Phe | Phe | Gly | Leu |
| | 50 | | | | | 55 | | | | | 60 | | | | |
| Gln | Tyr | Thr | Ile | Lys | Asp | Thr | Val | Ala | Trp | Leu | Lys | Met | Asp | Lys | Lys |
| 65 | | | | | 70 | | | | | 75 | | | | | 80 |
| Val | Leu | Asp | His | Asp | Val | Ser | Lys | Glu | Glu | Pro | Val | Thr | Phe | His | Phe |
| | | | | 85 | | | | | 90 | | | | | 95 | |
| Leu | Ala | Lys | Phe | Tyr | Pro | Glu | Asn | Ala | Glu | Glu | Leu | Val | Gln | Glu |
| | | | 100 | | | | | 105 | | | | | 110 | | |
| Ile | Thr | Gln | His | Leu | Phe | Phe | Leu | Gln | Val | Lys | Lys | Gln | Ile | Leu | Asp |
| | | | 115 | | | | | 120 | | | | | 125 | | |
| Glu | Lys | Val | Tyr | Cys | Pro | Pro | Glu | Ala | Ser | Val | Leu | Leu | Ala | Ser | Tyr |
| | | 130 | | | | | 135 | | | | | 140 | | | |
| Ala | Val | Gln | Ala | Lys | Tyr | Gly | Asp | Tyr | Asp | Pro | Ser | Val | His | Lys | Arg |
| 145 | | | | | 150 | | | | | 155 | | | | | 160 |
| Gly | Phe | Leu | Ala | Gln | Glu | Glu | Leu | Leu | Pro | Lys | Arg | Val | Ile | Asn | Leu |
| | | | | 165 | | | | | 170 | | | | | 175 | |
| Tyr | Gln | Met | Thr | Pro | Glu | Met | Trp | Glu | Glu | Arg | Ile | Thr | Ala | Trp | Tyr |
| | | | 180 | | | | | 185 | | | | | 190 | | |
| Ala | Glu | His | Arg | Gly | Arg | Ala | Arg | Asp | Glu | Ala | Glu | Met | Glu | Tyr | Leu |
| | | 195 | | | | | 200 | | | | | 205 | | | |

```
Lys  Ile  Ala  Gln  Asp  Leu  Glu  Met  Tyr  Gly  Val  Asn  Tyr  Phe  Thr  Ile
     210                 215                      220

Arg  Asn  Lys  Lys  Gly  Thr  Glu  Leu  Leu  Leu  Gly  Val  Asp  Ala  Leu  Gly
225                      230                 235                           240

Leu  His  Ile  Tyr  Asp  Pro  Glu  Asn  Arg  Leu  Thr  Pro  Lys  Ile  Ser  Phe
                    245                      250                 255

Pro  Trp  Asn  Glu  Ile  Arg  Asn  Ile  Ser  Tyr  Ser  Asp  Lys  Glu  Phe  Thr
               260                      265                      270

Ile  Lys  Pro  Leu  Asp  Lys  Lys  Ile  Asp  Val  Phe  Lys  Phe  Asp  Ser  Ser
          275                      280                 285

Lys  Leu  Arg  Val  Asn  Lys  Leu  Ile  Leu  Gln  Leu  Cys  Ile  Gly  Asn  His
     290                      295                 300

Asp  Leu  Phe  Met  Arg  Arg  Lys  Ala  Asp  Ser  Leu  Glu  Val  Gln  Gln
305                      310                 315                      320

Met  Lys  Ala  Gln  Ala  Arg  Glu  Glu  Lys  Ala  Arg  Lys  Gln  Met  Glu  Arg
                    325                      330                 335

Gln  Arg  Leu  Ala  Arg  Glu  Lys  Gln  Met  Arg  Glu  Glu  Ala  Glu  Arg  Thr
               340                      345                 350

Arg  Asp  Glu  Leu  Glu  Arg  Arg  Leu  Leu  Gln  Met  Lys  Glu  Glu  Ala  Thr
          355                      360                 365

Met  Ala  Asn  Glu  Ala  Leu  Met  Arg  Ser  Glu  Glu  Thr  Ala  Asp  Leu  Leu
370                      375                 380

Ala  Glu  Lys  Ala  Gln  Ile  Thr  Glu  Glu  Glu  Ala  Lys  Leu  Leu  Ala  Gln
385                      390                 395                           400

Lys  Ala  Ala  Glu  Ala  Glu  Gln  Glu  Met  Gln  Arg  Ile  Lys  Ala  Thr  Ala
                    405                      410                 415

Ile  Arg  Thr  Glu  Glu  Lys  Arg  Leu  Met  Glu  Gln  Lys  Val  Leu  Glu
               420                      425                 430

Ala  Glu  Val  Leu  Ala  Leu  Asn  Met  Ala  Glu  Glu  Ser  Glu  Arg  Arg  Ala
          435                      440                 445

Lys  Glu  Ala  Asp  Gln  Leu  Lys  Gln  Asp  Leu  Gln  Glu  Ala  Arg  Glu  Ala
     450                      455                 460

Glu  Arg  Arg  Ala  Lys  Gln  Lys  Leu  Leu  Glu  Ile  Ala  Thr  Lys  Pro  Thr
465                      470                 475                           480

Tyr  Pro  Pro  Met  Asn  Pro  Ile  Pro  Pro  Leu  Pro  Pro  Asp  Ile  Pro
                    485                      490                 495

Ser  Phe  Asp  Ile  Ile  Ala  Asp  Ser  Leu  Ser  Phe  Asp  Phe  Lys  Asp  Thr
               500                      505                 510

Asp  Met  Lys  Arg  Leu  Ser  Met  Glu  Ile  Glu  Lys  Glu  Lys  Val  Glu  Tyr
          515                      520                 525

Met  Glu  Lys  Ser  Lys  His  Leu  Gln  Glu  Gln  Leu  Asn  Glu  Leu  Lys  Thr
     530                      535                 540

Glu  Ile  Glu  Ala  Leu  Lys  Leu  Lys  Glu  Arg  Glu  Thr  Ala  Leu  Asp  Val
545                      550                 555                           560

Leu  His  Ser  Glu  Ser  Ser  Asp  Arg  Gly  Gly  Pro  Ser  Ser  Lys  His  Asp
               565                      570                 575

Thr  Ile  Lys  Lys  Pro  Gln  Ala  Gln  Gly  Arg  Arg  Pro  Ile  Cys  Ile
          580                      585                 590
```

( 2 ) INFORMATION FOR SEQ ID NO:6:

( i ) SEQUENCE CHARACTERISTICS:
    ( A ) LENGTH: 1833 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: murine ( x i ) SEQUENCE DESCRIPTION: SEQ ID NO:6:

| | | | | | | |
|---|---|---|---|---|---|---|
| GCGCCCGGTA | CCTCGCGATG | GCCGGAGCCA | TCGCTTCTCG | CATGAGCTTC | AGCTCACTCA | 60 |
| AGAGGAAGCA | GCCCAAGACA | TTCACGGTGC | GGATCGTCAC | CATGGACGCC | GAGATGGAGT | 120 |
| TCAACTGCGA | GATGAAATGG | AAGGGGAAGG | ACCTGTTTGA | TTTGGTGTGC | CGGACACTGG | 180 |
| GGCTTCGGGA | AACCTGGTTC | TTTGGACTGC | AGTATACAAT | CAAGGACACG | GTGGCCTGGC | 240 |
| TCAAAATGGA | CAAGAAGGTG | TTGGATCATG | ATGTTTCGAA | GGAAGAACCA | GTTACCTTTC | 300 |
| ACTTCCTGGC | CAAATTTTAT | CCTGAAAATG | CTGAGGAGGA | GCTAGTTCAA | GAGATCACGC | 360 |
| AACACTTATT | TTTCTTACAG | GTGAAGAAGC | AGATTTTGGA | TGAAAAGGTC | TACTGCCCTC | 420 |
| CCGAGGCGTC | CGTGCTCTTG | GCGTCATATG | CTGTCCAGGC | CAAGTATGGC | GACTATGACC | 480 |
| CCTCTGTGCA | CAAGCGGGGA | TTTTTAGCCC | AAGAGGAATT | GCTCCCGAAA | AGGGTGATAA | 540 |
| ATCTCTATCA | GATGACTCCG | GAAATGTGGG | AGGAGAGAAT | TACGGCTTGG | TATGCGGAGC | 600 |
| ACCGGGGCAG | AGCCAGGGAT | GAAGCTGAAA | TGGAGTATTT | GAAGATAGCT | CAGGACCTGG | 660 |
| AGATGTATGG | TGTGAACTAC | TTTACAATCC | GGAATAAAAA | GGGCACAGAG | TTGCTGCTTG | 720 |
| GAGTGGATGC | TCTTGGGCTT | CATATCTATG | ACCCTGAGAA | CAGGCTGACC | CCCAAGATCT | 780 |
| CCTTCCCATG | GAATGAAATC | CGAAACATCT | CCTACAGCGA | CAAGGAGTTT | ACTATTAAAC | 840 |
| CACTGGATAA | GAAAATTGAT | GTCTTCAAAT | TTAACTCCTC | AAAGCTTCGT | GTTAATAAGC | 900 |
| TGATTCTTCA | GCTATGTATT | GGGAACCATG | ACCTATTTAT | GAGGCGACGG | AAAGCTGACT | 960 |
| CTTTAGAAGT | TCAGCAGATG | AAAGCCCAGG | CCAGGGAAGA | GAAGGCTAGA | AAGCAGATGG | 1020 |
| AAAGGCAGCG | GCTGGCTCGA | GAGAAGCAGA | TGCGGGAGGA | GGCCGAGCGT | ACAAGAGATG | 1080 |
| AGTTAGAGAG | GAGGCTCCTG | CAGATGAAAG | AAGAAGCAAC | GATGGCCAAT | GAAGCTCTGA | 1140 |
| TGCGCTCTGA | GGAGACAGCT | GATCTGTTGG | CTGAAAAGGC | TCAGATCACA | GAGGAGGAGG | 1200 |
| CCAAGCTTTT | GGCACAAAAG | CTGCAGAGG | CTGAGCAAGA | GATGCAGCGA | ATCAAGGCCA | 1260 |
| CGGCCATTCG | GACAGAGGAG | GAGAAGCGCC | TGATGGAGCA | GAAGGTGCTG | GAGGCTGAAG | 1320 |
| TGCTGGCATT | GAACATGGCT | GAGGAGTCAG | AGAGGAGGGC | CAAGGAGGCT | GATCAGTTAA | 1380 |
| AGCAAGACTT | GCAAGAAGCC | AGAGAAGCAG | AGCGAAGAGC | CAAGCAGAAG | CTCTTAGAAA | 1440 |
| TCGCCACCAA | GCCCACCTAT | CCACCCATGA | ACCCAATTCC | ACCACCACTG | CCTCCTGACA | 1500 |
| TACCGAGCTT | CGACATTATT | GCTGACAGCT | TGTCATTCGA | CTTCAAGGAT | ACGGACATGA | 1560 |
| AGCGACTTTC | CATGGAGATA | GAGAAAGAAA | AAGTGGAGTA | CATGGAGAAG | AGCAAGCACC | 1620 |
| TGCAGGAGCA | GCTCAACGAG | CTCAAGACGG | AGATCGAGGC | CTTGAAACTC | AAAGAGCGGG | 1680 |
| AGACGGCCTT | GGACGTCCTA | CACAGCGAGA | GCTCAGACAG | AGGCGGCCCC | AGCAGCAAGC | 1740 |
| ATAATACCAT | TAAAAAGGTA | CCTGAAATGT | GAGCTCACTC | TGCAGAGCGC | CAAGTCCCGA | 1800 |
| GTGGCCTTCT | TTGAAGAACT | CTAGCAGGTG | ACC | | | 1833 |

( 2 ) INFORMATION FOR SEQ ID NO:7:

( i ) SEQUENCE CHARACTERISTICS:
        ( A ) LENGTH: 584 amino acids
        ( B ) TYPE: amino acid ( D ) TOPOLOGY: linear ( i i ) MOLECULE TYPE: protein ( v ) FRAGMENT TYPE: N-terminal ( v i ) ORIGINAL SOURCE:
  ( A ) ORGANISM: murine ( x i ) SEQUENCE DESCRIPTION: SEQ ID NO:7:

| Met | Ala | Gly | Ala | Ile | Ala | Ser | Arg | Met | Ser | Phe | Ser | Ser | Leu | Lys | Arg |
|---|---|---|---|---|---|---|---|---|---|---|---|---|---|---|---|
| 1 | | | | 5 | | | | | 10 | | | | | 15 | |

| Lys | Gln | Pro | Lys | Thr | Phe | Thr | Val | Arg | Ile | Val | Thr | Met | Asp | Ala | Glu |
|---|---|---|---|---|---|---|---|---|---|---|---|---|---|---|---|
| | | | 20 | | | | | 25 | | | | | 30 | | |

| Met | Glu | Phe | Asn | Cys | Glu | Met | Lys | Trp | Lys | Gly | Lys | Asp | Leu | Phe | Asp |
|---|---|---|---|---|---|---|---|---|---|---|---|---|---|---|---|
| | | | 35 | | | | 40 | | | | | 45 | | | |

| Leu | Val | Cys | Arg | Thr | Leu | Gly | Leu | Arg | Asp | Thr | Trp | Phe | Phe | Gly | Leu |
|---|---|---|---|---|---|---|---|---|---|---|---|---|---|---|---|
| | 50 | | | | | 55 | | | | | 60 | | | | |

| Gln | Tyr | Thr | Ile | Lys | Asp | Thr | Val | Ala | Trp | Leu | Lys | Met | Asp | Lys | Lys |
|---|---|---|---|---|---|---|---|---|---|---|---|---|---|---|---|
| 65 | | | | | 70 | | | | 75 | | | | | | 80 |

| Val | Leu | Asp | His | Asp | Val | Ser | Lys | Glu | Glu | Pro | Val | Thr | Phe | His | Phe |
|---|---|---|---|---|---|---|---|---|---|---|---|---|---|---|---|
| | | | | 85 | | | | | 90 | | | | | 95 | |

| Leu | Ala | Lys | Phe | Tyr | Pro | Glu | Asn | Ala | Glu | Glu | Leu | Val | Gln | Glu |
|---|---|---|---|---|---|---|---|---|---|---|---|---|---|---|
| | | | 100 | | | | | 105 | | | | 110 | | |

| Ile | Thr | Gln | His | Leu | Phe | Phe | Leu | Gln | Val | Lys | Lys | Glu | Ile | Leu | Asp |
|---|---|---|---|---|---|---|---|---|---|---|---|---|---|---|---|
| | | | 115 | | | | | 120 | | | | 125 | | | |

| Glu | Lys | Val | Tyr | Cys | Pro | Pro | Glu | Ala | Ser | Val | Leu | Leu | Ala | Ser | Tyr |
|---|---|---|---|---|---|---|---|---|---|---|---|---|---|---|---|
| | 130 | | | | | 135 | | | | | 140 | | | | |

| Ala | Val | Gln | Ala | Lys | Tyr | Gly | Asp | Tyr | Asp | Pro | Ser | Val | His | Lys | Arg |
|---|---|---|---|---|---|---|---|---|---|---|---|---|---|---|---|
| 145 | | | | | 150 | | | | | 155 | | | | | 160 |

| Gly | Phe | Leu | Ala | Gln | Glu | Glu | Leu | Leu | Pro | Lys | Arg | Val | Ile | Asn | Leu |
|---|---|---|---|---|---|---|---|---|---|---|---|---|---|---|---|
| | | | | 165 | | | | | 170 | | | | | 175 | |

| Tyr | Gln | Met | Thr | Pro | Glu | Met | Trp | Glu | Glu | Arg | Ile | Thr | Ala | Trp | Tyr |
|---|---|---|---|---|---|---|---|---|---|---|---|---|---|---|---|
| | | | 180 | | | | | 185 | | | | | 190 | | |

| Ala | Glu | His | Arg | Gly | Arg | Ala | Arg | Asp | Glu | Ala | Glu | Met | Glu | Tyr | Leu |
|---|---|---|---|---|---|---|---|---|---|---|---|---|---|---|---|
| | | | 195 | | | | | 200 | | | | | 205 | | |

| Lys | Ile | Ala | Gln | Asp | Leu | Glu | Met | Tyr | Gly | Val | Asn | Tyr | Phe | Thr | Ile |
|---|---|---|---|---|---|---|---|---|---|---|---|---|---|---|---|
| | 210 | | | | | 215 | | | | | 220 | | | | |

| Arg | Asn | Lys | Lys | Gly | Thr | Glu | Leu | Leu | Leu | Gly | Val | Asp | Ala | Leu | Gly |
|---|---|---|---|---|---|---|---|---|---|---|---|---|---|---|---|
| 225 | | | | | 230 | | | | | 235 | | | | | 240 |

| Leu | His | Ile | Tyr | Asp | Pro | Glu | Asn | Arg | Leu | Thr | Pro | Lys | Ile | Ser | Phe |
|---|---|---|---|---|---|---|---|---|---|---|---|---|---|---|---|
| | | | | 245 | | | | | 250 | | | | | 255 | |

| Pro | Trp | Asn | Glu | Ile | Arg | Asn | Ile | Ser | Tyr | Ser | Asp | Lys | Glu | Phe | Thr |
|---|---|---|---|---|---|---|---|---|---|---|---|---|---|---|---|
| | | | 260 | | | | | 265 | | | | | 270 | | |

| Ile | Lys | Pro | Leu | Asp | Lys | Lys | Ile | Asp | Val | Phe | Lys | Phe | Asp | Ser | Ser |
|---|---|---|---|---|---|---|---|---|---|---|---|---|---|---|---|
| | | 275 | | | | | 280 | | | | | 285 | | | |

| Lys | Leu | Arg | Val | Asn | Lys | Leu | Ile | Leu | Gln | Leu | Cys | Ile | Gly | Asn | His |
|---|---|---|---|---|---|---|---|---|---|---|---|---|---|---|---|
| | 290 | | | | | 295 | | | | | 300 | | | | |

| Asp | Leu | Phe | Met | Arg | Arg | Arg | Lys | Ala | Asp | Ser | Leu | Glu | Val | Gln | Gln |
|---|---|---|---|---|---|---|---|---|---|---|---|---|---|---|---|
| 305 | | | | | 310 | | | | | 315 | | | | | 320 |

| Met | Lys | Ala | Gln | Ala | Arg | Glu | Glu | Lys | Ala | Arg | Lys | Gln | Met | Glu | Arg |
|---|---|---|---|---|---|---|---|---|---|---|---|---|---|---|---|
| | | | | 325 | | | | | 330 | | | | | 335 | |

| Gln | Arg | Leu | Ala | Arg | Glu | Lys | Gln | Met | Arg | Glu | Glu | Ala | Glu | Arg | Thr |
|---|---|---|---|---|---|---|---|---|---|---|---|---|---|---|---|
| | | | 340 | | | | | 345 | | | | | 350 | | |

| Arg | Asp | Glu | Leu | Glu | Arg | Arg | Leu | Leu | Gln | Met | Lys | Glu | Glu | Ala | Thr |
|---|---|---|---|---|---|---|---|---|---|---|---|---|---|---|---|
| | | | 355 | | | | | 360 | | | | | 365 | | |

|   |   |   |   |   |   |   |   |   |   |   |   |   |   |   |
|---|---|---|---|---|---|---|---|---|---|---|---|---|---|---|
| Met | Ala | Asn | Glu | Ala | Leu | Met | Arg | Ser | Glu | Glu | Thr | Ala | Asp | Leu | Leu |
|  | 370 |  |  |  |  | 375 |  |  |  |  | 380 |  |  |  |  |
| Ala | Glu | Lys | Ala | Gln | Ile | Thr | Glu | Glu | Glu | Ala | Lys | Leu | Leu | Ala | Gln |
| 385 |  |  |  |  | 390 |  |  |  |  | 395 |  |  |  |  | 400 |
| Lys | Ala | Ala | Glu | Ala | Glu | Gln | Glu | Met | Gln | Arg | Ile | Lys | Ala | Thr | Ala |
|  |  |  |  | 405 |  |  |  |  | 410 |  |  |  |  | 415 |  |
| Ile | Arg | Thr | Glu | Glu | Glu | Lys | Arg | Leu | Met | Glu | Gln | Lys | Val | Leu | Glu |
|  |  |  | 420 |  |  |  |  | 425 |  |  |  |  | 430 |  |  |
| Ala | Glu | Val | Leu | Ala | Leu | Asn | Met | Ala | Glu | Ser | Glu | Arg | Arg | Ala |
|  |  | 435 |  |  |  |  | 440 |  |  |  |  | 445 |  |  |  |
| Lys | Glu | Ala | Asp | Gln | Leu | Lys | Gln | Asp | Leu | Gln | Glu | Ala | Arg | Glu | Ala |
|  | 450 |  |  |  |  | 455 |  |  |  |  | 460 |  |  |  |  |
| Glu | Arg | Arg | Ala | Lys | Gln | Lys | Leu | Leu | Glu | Ile | Ala | Thr | Lys | Pro | Thr |
| 465 |  |  |  |  | 470 |  |  |  |  | 475 |  |  |  |  | 480 |
| Tyr | Pro | Pro | Met | Asn | Pro | Ile | Pro | Pro | Leu | Pro | Pro | Asp | Ile | Pro |
|  |  |  |  | 485 |  |  |  |  | 490 |  |  |  |  | 495 |  |
| Ser | Phe | Asp | Ile | Ile | Ala | Asp | Ser | Leu | Ser | Phe | Asp | Phe | Lys | Asp | Thr |
|  |  |  | 500 |  |  |  |  | 505 |  |  |  |  | 510 |  |  |
| Asp | Met | Lys | Arg | Leu | Ser | Met | Glu | Ile | Glu | Lys | Glu | Lys | Val | Glu | Tyr |
|  |  | 515 |  |  |  |  | 520 |  |  |  |  | 525 |  |  |  |
| Met | Glu | Lys | Ser | Lys | His | Leu | Gln | Glu | Gln | Leu | Asn | Glu | Leu | Lys | Thr |
|  | 530 |  |  |  |  | 535 |  |  |  |  | 540 |  |  |  |  |
| Glu | Ile | Glu | Ala | Leu | Lys | Leu | Lys | Glu | Arg | Glu | Thr | Ala | Leu | Asp | Val |
| 545 |  |  |  |  | 550 |  |  |  |  | 555 |  |  |  |  | 560 |
| Leu | His | Ser | Glu | Ser | Ser | Asp | Arg | Gly | Gly | Pro | Ser | Ser | Lys | His | Asp |
|  |  |  |  | 565 |  |  |  |  | 570 |  |  |  |  | 575 |  |
| Thr | Ile | Lys | Lys | Val | Pro | Glu | Met |
|  |  |  | 580 |

( 2 ) INFORMATION FOR SEQ ID NO:8:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapien ( x i ) SEQUENCE DESCRIPTION: SEQ ID NO:8:

AAGCTCACCT TGCAGAGCGC CAAGTCCCGA GTGGCCTTCT TGAAGAGCT CTAG    54

( 2 ) INFORMATION FOR SEQ ID NO:9:

( i ) SEQUENCE CHARACTERISTICS:
        ( A ) LENGTH: 2080 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:

(A) ORGANISM: Homo sapien (xi) SEQUENCE DESCRIPTION: SEQ ID NO:9:

```
ACGGCAGCCG TCAGGGACCT GCCCCAACT  CCCCTTTCCG CTCAGGCAGG GTCCTCGCGG      60
CCCATGCTGG CCGCTGGGGA CCCGCGCAGC CCAGACCGTT CCCGGGCCGG CCAGCCGGCA     120
CCATGGTGGC CCTGAGGCCT GTGCAGCAAC TCCAGGGGGG CTAAAGGGCT CAGAGTGCAG     180
GCCGTGGGGC GCGAGGGTCC CGGGCCTGAG CCCCGCGCCA TGGCCGGGGC CATCGCTTCC     240
CGCATGAGCT TCAGCTCTCT CAAGAGGAAG CAACCCAAGA CGTTCACCGT GAGGATCGTC     300
ACCATGGACG CCGAGATGGA GTTCAATTGC GAGATGAAGT GGAAGGGAA  GGACCTCTTT     360
GATTTGGTGT GCCGGACTCT GGGGCTCCGA GAAACCTGGT CTTTGGACT  GCAGTACACA     420
ATCAAGGACA CAGTGGCCTG GCTCAAAATG GACAAGAAGG TACTGGATCA TGATGTTTCA     480
AAGGAAGAAC CAGTCACCTT TCACTTCTTG GCCAAATTTT ATCCTGAGAA TGCTGAAGAG     540
GAGCTGGTTC AGGAGATCAC ACAACATTTA TTCTTCTTAC AGGTAAAGAA GCAGATTTTA     600
GATGAAAAGA TCTACTGCCC TCCTGAGGCT CTGTGCTCC  TGGCTTCTTA CGCCGTCCAG     660
GCCAAGTATG GTGACTACGA CCCCAGTGTT CACAAGCGGG ATTTTGGC   CCAAGAGGAA     720
TTGCTTCCAA AAGGGTAAT  AAATCTGTAT CAGATGACTC CGGAAATGTG GAGGAGAGA     780
ATTACTGCTT GGTACGCAGA GCACCGAGGC CGAGCCAGGG ATGAAGCTGA AATGGAATAT     840
CTGAAGATAG CTCAGGACCT GGAGATGTAC GGTGTGAACT ACTTTGCAAT CCGGAATAAA     900
AAGGGCACAG AGCTGCTGCT GGAGTGGAT  GCCCTGGGGC TTCACATTTA TGACCCTGAG     960
AACAGACTGA CCCCCAAGAT CTCCTTCCCG TGGAATGAAA TCCGAAACAT CTCGTACAGT    1020
GACAAGGAGT TTACTATTAA ACCACTGGAT AAGAAAATTG ATGTCTTCAA GTTTAACTCC    1080
TCAAAGCTTC GTGTTAATAA GCTGATTCTC CAGCTATGTA TCGGGAACCA TGATCTATTT    1140
ATGAGGAGAA GGAAAGCCGA TTCTTTGGAA GTTCAGCAGA TGAAAGCCCA GGCCAGGGAG    1200
GAGAAGGCTA GAAAGCAGAT GGAGCGGCAG CGCCTCGCTC GAGAGAAGCA GATGAGGGAG    1260
GAGGCTGAAC GCACGAGGGA TGAGTTGGAG AGGAGGCTGC TGCAGATGAA AGAAGAAGCA    1320
ACAATGGCCA ACGAAGCACT GATGCGGTCT GAGGAGACAG CTGACCTGTT GGCTGAAAAG    1380
GCCCAGATCA CCGAGGAGGA GGCAAAACTT CTGGCCCAGA AGGCCGCAGA GGCTGAGCAG    1440
GAAATGCAGC GCATCAAGGC CACAGCGATT CGCACGGAGG AGGAGAAGCG CCTGATGGAG    1500
CAGAAGGTGC TGGAAGCCGA GGTGCTGGCA CTGAAGATGG CTGAGGAGTC AGAGAGGAGG    1560
GCCAAAGAGG CAGATCAGCT GAAGCAGGAC CTGCAGGAAG CACGCGAGGC GGAGCGAAGA    1620
GCCAAGCAGA AGCTCCTGGA GATTGCCACC AAGCCCACGT ACCCGCCCAT GAACCCAATT    1680
CCAGCACCGT TGCCTCCTGA CATACCAAGC TTCAACCTCA TTGGTGACAG CCTGTCTTTC    1740
GACTTCAAAG ATACTGACAT GAAGCGGCTT CCATGGAGA  TAGAGAAAGA AAAAGTGGAA    1800
TACATGGAAA AGAGCAAGCA TCTGCAGGAG CAGCTCAATG AACTCAAGAC AGAAATCGAG    1860
GCCTTGAAAC TGAAAGAGAG GGAGACAGCT CTGGATATTC TGCACAATGA GAACTCCGAC    1920
AGGGGTGGCA GCAGCAAGCA CAATACCATT AAAAAGCCTC AAGCCCAAGG CAGAAGACCT    1980
ATCTGCATTT GAGCCCTCAA ACTCACCTTG CAGAGCGCCA AGTCCGAGT  GGCCTTCTTT    2040
GAAGAGCTCT AGCAGGTGAC CCAGCCACCC CAGGACCTGC                          2080
```

(2) INFORMATION FOR SEQ ID NO:10:

(i) SEQUENCE CHARACTERISTICS:
(A) LENGTH: 591 amino acids
(B) TYPE: amino acid ( D ) TOPOLOGY: linear ( i i ) MOLECULE TYPE: protein ( v ) FRAGMENT TYPE: N-terminal ( v i ) ORIGINAL SOURCE:
    ( A ) ORGANISM: Homo sapien ( x i ) SEQUENCE DESCRIPTION: SEQ ID NO:10:

```
Met  Ala  Gly  Ala  Ile  Ala  Ser  Arg  Met  Ser  Phe  Ser  Ser  Leu  Lys  Arg
1                    5                        10                       15

Lys  Gln  Pro  Lys  Thr  Phe  Thr  Val  Arg  Ile  Val  Thr  Met  Asp  Ala  Glu
              20                       25                       30

Met  Glu  Phe  Asn  Cys  Glu  Met  Lys  Trp  Lys  Gly  Lys  Asp  Leu  Phe  Asp
          35                        40                       45

Leu  Val  Cys  Arg  Thr  Leu  Gly  Leu  Arg  Glu  Thr  Trp  Phe  Phe  Gly  Leu
     50                       55                       60

Gln  Tyr  Thr  Ile  Lys  Asp  Thr  Val  Ala  Trp  Leu  Lys  Met  Asp  Lys  Lys
65                       70                       75                       80

Val  Leu  Asp  His  Asp  Val  Ser  Lys  Glu  Glu  Pro  Val  Thr  Phe  His  Phe
               85                       90                       95

Leu  Ala  Lys  Phe  Tyr  Pro  Glu  Asn  Ala  Glu  Glu  Leu  Val  Gln  Glu
               100                      105                      110

Ile  Thr  Gln  His  Leu  Phe  Phe  Leu  Gln  Val  Lys  Lys  Gln  Ile  Leu  Asp
               115                      120                      125

Glu  Lys  Ile  Tyr  Cys  Pro  Pro  Glu  Ala  Ser  Val  Leu  Leu  Ala  Ser  Tyr
     130                      135                      140

Ala  Val  Gln  Ala  Lys  Tyr  Gly  Asp  Tyr  Asp  Pro  Ser  Val  His  Lys  Arg
145                      150                      155                      160

Gly  Phe  Leu  Ala  Gln  Glu  Glu  Leu  Leu  Pro  Lys  Arg  Val  Ile  Asn  Leu
               165                      170                      175

Tyr  Gln  Met  Thr  Pro  Glu  Met  Trp  Glu  Glu  Arg  Ile  Thr  Ala  Trp  Tyr
               180                      185                      190

Ala  Glu  His  Arg  Gly  Arg  Ala  Arg  Asp  Glu  Ala  Glu  Met  Glu  Tyr  Leu
          195                      200                      205

Lys  Ile  Ala  Gln  Asp  Leu  Glu  Met  Tyr  Gly  Val  Asn  Tyr  Phe  Ala  Ile
     210                      215                      220

Arg  Asn  Lys  Lys  Gly  Thr  Glu  Leu  Leu  Leu  Gly  Val  Asp  Ala  Leu  Gly
225                      230                      235                      240

Leu  His  Ile  Tyr  Asp  Pro  Glu  Asn  Arg  Leu  Thr  Pro  Lys  Ile  Ser  Phe
               245                      250                      255

Pro  Trp  Asn  Glu  Ile  Arg  Asn  Ile  Ser  Tyr  Ser  Asp  Lys  Glu  Phe  Thr
               260                      265                      270

Ile  Lys  Pro  Leu  Asp  Lys  Lys  Ile  Asp  Val  Phe  Lys  Phe  Asn  Ser  Ser
          275                      280                      285

Lys  Leu  Arg  Val  Asn  Lys  Leu  Ile  Leu  Gln  Leu  Cys  Ile  Gly  Asn  His
     290                      295                      300

Asp  Leu  Phe  Met  Arg  Arg  Arg  Lys  Ala  Asp  Ser  Leu  Glu  Val  Gln  Gln
305                      310                      315                      320

Met  Lys  Ala  Gln  Ala  Arg  Glu  Glu  Lys  Ala  Arg  Lys  Gln  Met  Glu  Arg
               325                      330                      335

Gln  Arg  Leu  Ala  Arg  Glu  Lys  Gln  Met  Arg  Glu  Glu  Ala  Glu  Arg  Thr
               340                      345                      350

Arg  Asp  Glu  Leu  Glu  Arg  Arg  Leu  Gln  Met  Lys  Glu  Ala  Thr
               355                      360                      365
```

```
Met  Ala  Asn  Glu  Ala  Leu  Met  Arg  Ser  Glu  Glu  Thr  Ala  Asp  Leu  Leu
     370                      375                      380
Ala  Glu  Lys  Ala  Gln  Ile  Thr  Glu  Glu  Glu  Ala  Lys  Leu  Leu  Ala  Gln
385                      390                      395                      400
Lys  Ala  Ala  Glu  Ala  Glu  Gln  Glu  Met  Gln  Arg  Ile  Lys  Ala  Thr  Ala
                    405                      410                      415
Ile  Arg  Thr  Glu  Glu  Glu  Lys  Arg  Leu  Met  Glu  Gln  Lys  Val  Leu  Glu
               420                      425                      430
Ala  Glu  Val  Leu  Ala  Leu  Lys  Met  Ala  Glu  Glu  Ser  Glu  Arg  Arg  Ala
          435                      440                      445
Lys  Glu  Ala  Asp  Gln  Leu  Lys  Gln  Asp  Leu  Gln  Glu  Ala  Arg  Glu  Ala
     450                      455                      460
Glu  Arg  Arg  Ala  Lys  Gln  Lys  Leu  Leu  Glu  Ile  Ala  Thr  Lys  Pro  Thr
465                      470                      475                      480
Tyr  Pro  Pro  Met  Asn  Pro  Ile  Pro  Ala  Pro  Leu  Pro  Pro  Asp  Ile  Pro
                    485                      490                      495
Ser  Phe  Asn  Leu  Ile  Gly  Asp  Ser  Leu  Ser  Phe  Asp  Phe  Lys  Asp  Thr
               500                      505                      510
Asp  Met  Lys  Arg  Leu  Ser  Met  Glu  Ile  Glu  Lys  Glu  Lys  Val  Glu  Tyr
          515                      520                      525
Met  Glu  Lys  Ser  Lys  His  Leu  Gln  Glu  Gln  Leu  Asn  Glu  Leu  Lys  Thr
     530                      535                      540
Glu  Ile  Glu  Ala  Leu  Lys  Leu  Lys  Glu  Arg  Glu  Thr  Ala  Leu  Asp  Ile
545                      550                      555                      560
Leu  His  Asn  Glu  Asn  Ser  Asp  Arg  Gly  Gly  Pro  Ser  Ser  Lys  His  Asn
                    565                      570                      575
Thr  Ile  Lys  Lys  Pro  Gln  Ala  Gln  Gly  Arg  Arg  Pro  Ile  Cys  Ile
               580                      585                      590
```

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CATGGCCGGG CCATCGCTTC C                                      21

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CCTGAACCAG CTCCTCTTCA GC                                   22

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:13:

TCAAAGGAAG AACCAGTCAC C    21

( 2 ) INFORMATION FOR SEQ ID NO:14:

(  i  ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:14:

TCAGCTTCAT CCCTGGCTCG    20

( 2 ) INFORMATION FOR SEQ ID NO:15:

(  i  ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:15:

GGAGAGAATT ACTGCTTGGT AC    22

( 2 ) INFORMATION FOR SEQ ID NO:16:

(  i  ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:16:

CATAAATAGA TCATGGTTCC CGAT    24

( 2 ) INFORMATION FOR SEQ ID NO:17:

(  i  ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:17:

CCTCAAAGCT TCGTGTTAAT AAGC    24

( 2 ) INFORMATION FOR SEQ ID NO:18:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: cDNA (  x i  ) SEQUENCE DESCRIPTION: SEQ ID NO:18:

TTCCTGCTCA GCCTCTGCGG C					21

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

GGAGGCAAAA CTTCTGGCCC AG					22

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

GACAGGCTGT CACCAATGAG G					21

( 2 ) INFORMATION FOR SEQ ID NO:21:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

CAATTCCAGC ACCGTTGCCT CC					22

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

GGGTGGCTGG GTCACCTGCT					20

( 2 ) INFORMATION FOR SEQ ID NO:23:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

GTGGAGTACA TGGAGAA					17

( 2 ) INFORMATION FOR SEQ ID NO:24:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:24:

TCTTCAAAGA AGGCCACTCG 20

( 2 ) INFORMATION FOR SEQ ID NO:25:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:25:

ACACAGCGAG AGCTCAGACA GA 22

( 2 ) INFORMATION FOR SEQ ID NO:26:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:26:

GAGGACTCAA ATGCAGATAG GTCT 24

NF2 ISOFORMS

TECHNICAL FIELD

The present invention relates generally to tumor suppressor proteins. More specifically, the invention pertains to novel human and mouse NF2 transcript isoforms.

BACKGROUND OF THE INVENTION

Neurofibromatosis type 2 (NF2) is an autosomal, dominantly inherited disorder characterized by multiple tumors of the central nervous system, predominantly bilateral vestibular schwannomas (acoustic neuromas) of the eighth cranial nerve. Other disease features include cranial meningiomas, spinal nerve root schwannomas and presenile lens opacities (Martuza et al. (1988) *N. Engl. J. Med.* 318:684–688; Kaiser-Kupfer et al. (1989) *Arch. Ophthalmol.* 107:541–544; Eldridge et al. (1991) *Am. J. Hum. Genet.* 49:133 (A676)).

The gene for NF2 has been mapped in the chromosomal region 22q12 between the loci D22S1 and D22S28. Experimenters have suggested that the gene acts as a tumor suppressor and that loss or inactivation of the gene therefore results in tumorigenesis (Seizinger et al. (1986) *Nature* 322:644–647; Seizinger et al. (1987) *Science* 236:317–319; Rouleau et al. (1987) *Nature* 329:246–248; Seizinger et al. (1987) *Proc. Natl. Acad. Sci. USA* 84:5419–5423; Wertelecki et al. (1988) *N. Engl. J. Med.* 319:278–283; Rouleau et al. (1990) *Am. J. Hum. Genet.* 46:323–328; Fontaine et al. (1991) *Genomics* 10:280–283; Wolff et al. (1992) *Am. J. Hum. Genet.* 51:478–485).

Recently, a candidate human NF2 gene was cloned and identified using physical mapping and positional cloning studies (Trofatter et al. (1993) *Cell* 72:791–800; Rouleau et al. (1993) *Nature* 363:515–521). Nonoverlapping DNA deletions in the NF2 gene region from three independent NF2 families and in mRNA from a meningioma in an unrelated NF2 patient, were demonstrated (Trofatter et al., supra). Germ-line and somatic mutations were also shown in DNA of the candidate human NF2 gene from both NF2 patients and NF2-related tumors, including sporadic meningiomas and vestibular schwannomas (Rouleau et al. (1993), supra).

The above-described NF2 gene, originally reported to encode a 587 amino acid protein, is now known to code for a protein having 595 amino acids, called merlin (for moesin-ezrin-radixin like protein). (The corrected NF2 cDNA sequence has been assigned GenBank Accession no. L11353). As evident by its name, the merlin protein exhibits significant homology to the moesin, ezrin and radixin proteins which are highly conserved. These proteins appear to be mediators between plasma membrane proteins and components of the cytoskeleton which regulate cell surface structure and dynamics, as well as cytoplasmic responses to growth factors and other external stimuli (Trofatter et al. supra; Rouleau et al. supra; Luna et al. (1992) *Science* 258:955–964). Among the family members, merlin shows the most extensive homology (65%) to moesin, ezrin and radixin within a region that spans approximately 340 residues at the N-terminus of the predicted protein (Trofatter et al. supra; Rouleau et al. (1993), supra). Cloning of the candidate NF2 gene was independently confirmed by Rouleau et al., who named the NF2-encoded gene product schwannomin (Rouleau et al. (1993), supra).

The NF2 gene is expressed in multiple tissues (Trofatter et al. supra), suggesting that alterations in this gene might be involved in the development of multiple tumor types in addition to the brain neoplasms typically associated with the inherited disorder. In this regard, cytogenetic and molecular studies have implicated losses in chromosome 22q in several human neoplasms (Seizinger et al. (1991) *Cytogenet. Cell Genet.* 58:1080–1096), including breast and colon carcinomas, glioblastomas, meningiomas, pheochromocytomas and schwannomas. This indicates that the NF2 gene may constitute a tumor suppressor gene of more general importance in tumorigenesis.

One of the methods by which varient gene products are produced is alternative splicing, a process whereby multiple transcripts are produced from a single gene. These transcript isoforms encode variant proteins with differing functions. In particular, the process yields distinct mRNAs which are often tissue-specific. Thus, the same gene can encode several proteins with differing functions, in a tissue-specific manner. In this regard, it has been suggested that alternative splicing in the C-terminal region of erythrocyte protein 4.1, a member of the moesin family, may be critical for its binding to the cytoskeletal protein, spectrin, and for the mechanical integrity of the red cell membrane (Discher et al. (1993) *J. Biol. Chem.* 268:7186–7195). However, such transcript isoforms have not heretofore been identified for the NF2 gene.

CLOSURES OF THE INVENTION

The present invention is based on the discovery of novel transcript isoforms of the human and mouse NF2 genes. The transcript isoforms and proteins encoded thereby are useful screening agents for diagnosing NF2 disease. The isoforms can also be used to probe tissue and tumor samples for the presence of related variants. The protein products of the transcript isoforms can be administered to cancerous tissues in order to suppress tumor growth. Similarly, cDNA from the transcript isoforms may be used in gene therapy applications. Since many of the transcript isoforms are tissue and/or tumor specific, antibodies raised against the proteins are useful tumor targeting agents.

Accordingly, in one embodiment, the invention is directed to an isolated protein encoded by an NF2 gene, other than the protein encoded by human NF2 transcript isoform I as depicted in FIGS. 1A–1C (SEQ ID NO:3).

In particularly preferred embodiments, the invention is directed to the proteins encoded by mouse NF2 isoforms I, II and III, as depicted in FIGS. 1A–1C (SEQ ID NOS:1 and 2) 2 (SEQ ID NO:4 an 5) and (SEQ ID NO:6 and 7) 3, respectively, as well as the protein encoded by human transcript isoform II, as depicted in FIGS. 7A–7D (SEQ ID NOS:9 and 10).

In additional embodiments, the invention is directed to antibodies reactive with these proteins.

In yet other embodiments, the invention is directed to isolated NF2 transcript isoforms encoding the above proteins.

In still further embodiments, the invention is directed to nucleic acid constructs comprising:

(a) the NF2 transcript isoforms; and (b) control sequences that are operably linked to the transcript isoforms whereby the transcript isoforms can be transcribed and translated in a host cell, and wherein at least one of the control sequences is heterologous to the transcript isoform.

In other embodiments, the subject invention is directed to host cells transformed with these constructs, and methods of recombinantly producing the NF2-encoded proteins.

These and other embodiments of the subject invention will readily occur to those of ordinary skill in the art in view of the disclosure herein.

BRIEF DESCRIPTION OF THE FIGURES

FIGS. 1A–1C depict the nucleotide sequence (SEQ ID NO:1) and deduced amino acid sequence (SEQ ID NO:2) of mouse NF2 cDNA derived from mouse transcript isoform I. The putative stop codon is indicated by an asterisk. The amino acid sequence (SEQ ID NO:3) of the human merlin protein (encoded by human transcript isoform I) is also shown. Dashes indicate positions of homology.

FIGS. 2A–2C depicts the nucleotide sequence (SEQ ID NO:4) and deduced amino acid sequence (SEQ ID NO:5) of mouse NF2 cDNA derived from mouse transcript isoform II. The putative stop codon is indicated by an asterisk.

FIGS. 3A–3C depicts the nucleotide sequence (SEQ ID NO:6) and deduced amino acid sequence (SEQ ID NO:7) of mouse NF2 cDNA derived from mouse transcript isoform III. The putative stop codon is indicated by an asterisk.

FIG. 4A depicts the 3' sequence of mouse NF2 transcript isoform II (SEQ ID NO:4). FIG. 4B depicts the 3' sequence of mouse NF2 transcript isoform III (SEQ ID NO:6).

FIGS. 7A–7D show the nucleotide sequence (SEQ ID NO:9) and deduced amino acid sequence (SEQ ID NO:10) of human NF2 cDNA derived from human transcript isoform II. The 45 bp insert is boxed and the premature termination codon is marked by three asterisks.

DETAILED DESCRIPTION

Figures 4A, 4B:
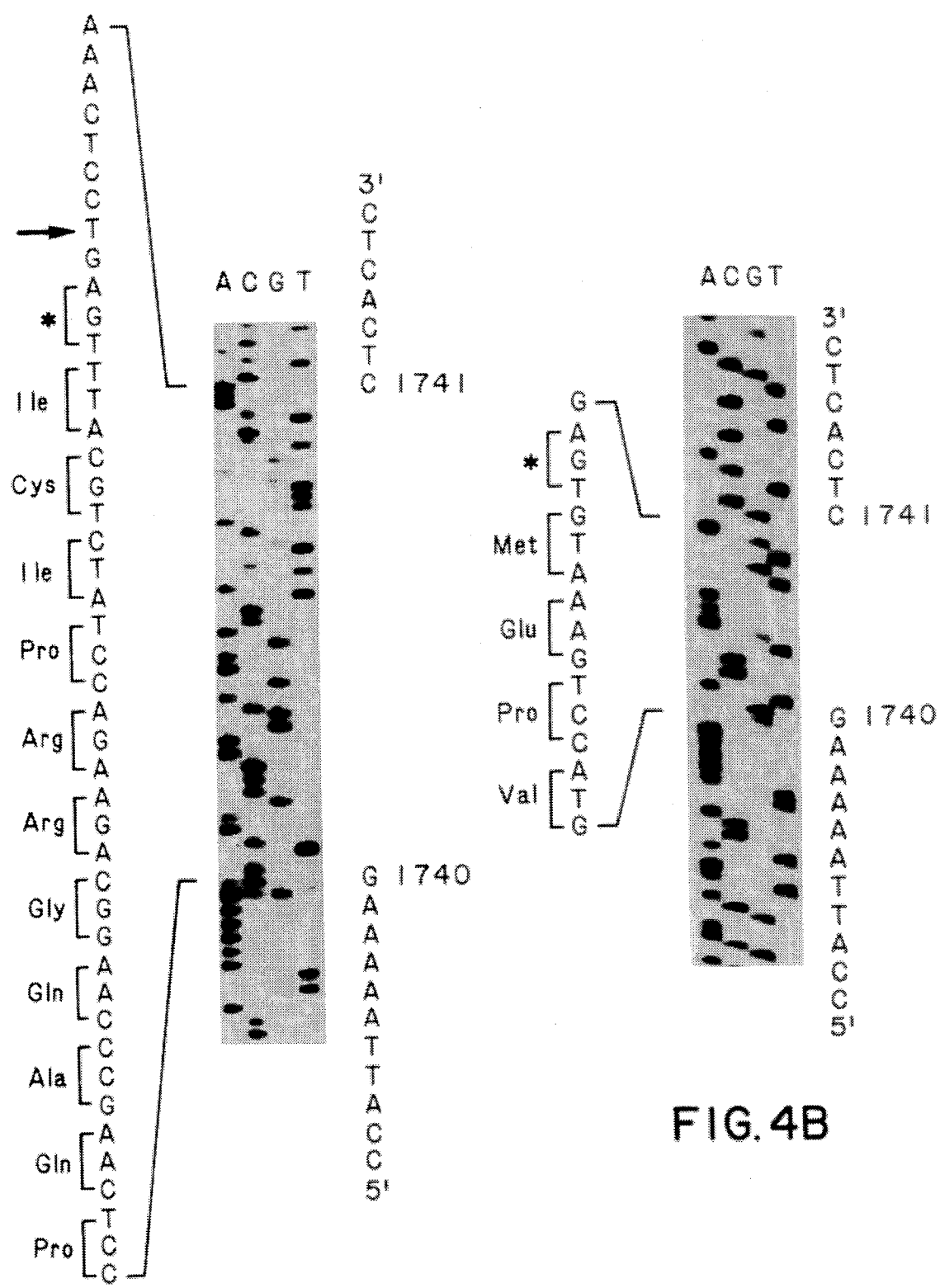
FIGS. 4A and 4B depict the partial nucleotide sequences and corresponding amino acid sequences at the 3' of mouse NF2 transcript isoforms II (SEQ ID NOS:4 and 5) and III (SEQ ID NO:6 and 7).

The practice of the present invention will employ, unless otherwise indicated, conventional techniques of molecular biology, microbiology and recombinant DNA technology, which are within the skill of the art. Such techniques are explained fully in the literature. See, e.g., Sambrook, Fritsch & Maniatis, *Molecular Cloning: A Laboratory Manual,* Second Edition (1989); *DNA Cloning,* Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

By "NF2 transcript isoform" is meant a nucleic acid molecule, including DNA, RNA, mRNA, cDNA derived from the mRNA, or even synthetic DNA, which is derived either directly or indirectly from an NF2 genomic sequence. As used herein, the term specifically excludes the NF2 gene encoding the merlin protein (GenBank Accession no. L11353), described in Trofatter et al. (1993) *Cell* 72:791–800, which codes for the human protein depicted in FIGS. 1A–1C (SEQ ID NO:3), termed "human NF2 transcript isoform I" herein. The term encompasses the entire genomic sequence including introns and exons. Alternatively, a transcript isoform can include transcripts of the genomic sequences which lack one or more introns or exons, or transcripts which incorporate noncoding or coding sequences, in addition to those found in the full-length, wild-type genomic sequence. Transcript isoforms may result from naturally occurring processing of the primary transcript of a gene, or from genetic engineering of nucleotide inserts, such as additions, deletions or substitutions, to yield a distinct protein coding sequence.

Transcript isoforms may or may not code for the same protein. The protein encoded by a transcript isoform may be shorter than the protein encoded by the full-length, wild-type gene, for example, due to the presence of premature stop codons or the deletion of a length of nucleotides. Alternatively, the isoforms may code for a protein longer than the protein encoded by the full-length, wild-type gene, for example, due to an insertion of nucleotides or due to a frameshift mutation resulting from an insertion or deletion, thus shifting the location of the stop codon downstream. Furthermore, a protein product of a transcript isoform may contain amino acids which differ from the wild-type protein due to an internal insertion of coding nucleotides or due to insertion of coding nucleotides upstream or downstream from the primary transcript.

Examples of transcript isoforms include, for example, human NF2 transcript isoform II (depicted in FIGS. 6 and 7A–7D) (SEQ ID NO:9), mouse NF2 transcript isoforms I, II and III (depicted in FIGS. 1, (SEQ ID NO:1) 2 (SEQ ID NO:4) and (SEQ ID NO:6) 3, respectively), as well as nucleotide sequences substantially homologous thereto.

These isoforms are described in more detail below. Thus, the term encompasses NF2 transcript isoforms derived from any mammalian species, as well as modifications, such as deletions, additions and substitutions, to these protein sequences. Such modifications of the sequences may result in proteins which have enhanced or decreased activity as compared to the wild-type sequence. These modifications may be deliberate, as through site-directed mutagenesis, or may be accidental, such as through naturally-occurring mutations. The term "transcript isoform" is used interchangeably with "alternative splice variant."

The term "NF2-encoded protein" denotes a protein encoded by an NF2 transcript isoform. Modifications to the resulting protein, such as by combination with other biological materials, such as lipids and saccharides, or by side chain modification, such as acetylation of amino groups, phosphorylation of hydroxyl side chains including phosphorylation of tyrosine, serine, threonine or any other side chains, or oxidation of sulfhydryl groups, as well as other modifications of the encoded primary sequence, are also captured by the term. Thus, included within the definition of "NF2-encoded protein" herein are glycosylated and unglycosylated forms, the amino acid sequences with or without associated phosphates, and amino acid sequences substantially homologous to the wild-type sequences.

By an "isolated protein" is meant a protein which is devoid of, in whole or part, tissue or cellular components with which the protein is normally associated in nature. Thus, a protein contained in a tissue extract would constitute an "isolated" protein, as would a protein synthetically or recombinantly produced. An "isolated" nucleotide sequence is a nucleotide sequence which has also been removed from the tissue or tumor in which it is normally found; or a sequence devoid, in whole or part, of sequences normally associated with it in nature; or a sequence, as it exists in nature, but having heterologous sequences (as defined below) in association therewith.

The term "isolated" does not denote the method by which the proteins or nucleic acid molecules are obtained or the level of purity of the preparations. Thus, such isolated species may be produced recombinantly, isolated directly from the cell or tissue of interest or produced synthetically based on the determined sequences.

Two nucleotide or polypeptide sequences are "substantially homologous" when at least about 85% (preferably at least about 85% to 90%, and most preferably at least about 95%) of the nucleotides or amino acids match over a defined length of the molecule. As used herein, substantially homologous also refers to sequences showing identity to the specified nucleotide or polypeptide sequence. Nucleotide sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

The terms "polypeptide" and "protein" are used interchangeably and refer to any polymer of amino acids (dipeptide or greater) linked through peptide bonds. Thus, the terms "polypeptide" and "protein" include oligopeptides, protein fragments, analogs, muteins, fusion proteins and the like.

By "antibody reactive with an NF2-encoded protein" is meant an antibody, either polyclonal or monoclonal, which is specific for an NF2-encoded protein, as defined above, or specific for a protein homologous thereto. Such reactivity can be determined by immunoprecipitation and Western blot analysis, using methods well known in the art. Such an antibody denotes not only the intact molecule, but also active fragments thereof, retaining specificity for the NF2-encoded protein in question. (See, e.g., Baldwin, R. W. et al. in *Monoclonal Antibodies for Cancer Detection and Therapy* (Academic Press 1985) for a description of the production of antibody fragments.) The term also contemplates chimeric antibodies that retain specificity for the NF2 protein in question. In particular, the antibody can include the variable regions or fragments of the variable regions which retain specificity for the NF2-encoded molecule. The remainder of the antibody can be derived from the species in which the antibody will be used. Thus, if the antibody is to be used in a human, the antibody can be "humanized" in order to reduce immunogenicity yet retain activity. For a description of chimeric antibodies, see, e.g., Winter, G. and Milstein, C. (1991) *Nature* 349:293–299; Jones et al. (1986) *Nature* 321:522–525; Riechmann et al. (1988) 332:323–327; and Carter et al. (1992) *Proc. Natl. Acad. Sci. USA* 89:4285–4289.

"Recombinant" as used herein to describe a polynucleotide means a polynucleotide of genomic, cDNA, mRNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines" "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

A DNA "coding sequence" or a "nucleotide sequence encoding" a particular protein, is a nucleotide sequence which is transcribed and translated into a polypeptide in vivo or in vitro when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, eucaryotic mRNA, cDNA from the mRNA, genomic DNA, and even synthetic RNA and DNA sequences. A transcription termination sequence will usually be located 3' to the coding sequence.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "heterologous" region of a nucleic acid construct is an identifiable segment of nucleic acid within or attached to another nucleic acid molecule that is not found in association with the other molecule in nature. Thus, when the heterologous region encodes an NF2 isoform, the region will usually be flanked by nucleic acid that does not flank the NF2 gene in the source genome. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

B. General Methods

Central to the present invention is the discovery of several NF2 transcript isoforms, identified in a variety of tissue and tumor types. These transcript isoforms represent differential processing of genomic DNA sequences, at the level of transcription, and result in variant proteins. The isoforms provide useful tools for the analysis of the normal function of tumor suppressor factors, such as the merlin protein, and also provide useful markers for the detection of NF2 disease. Additionally, since several of the NF2-encoded proteins are present in normal, noncancerous tissues and appear to function as tumor suppressors, the protein products of the transcript isoforms can be administered to cancerous tissues in order to suppress tumor growth. Similarly, cDNA from the transcript isoforms may be used in gene therapy applications. Since many of the transcript isoforms are tissue and/or tumor specific, antibodies raised against the proteins are useful tumor targeting agents.

In particular, at least two human NF2 transcript isoforms have been identified and characterized, using RNA polymerase chain reaction (PCR) and single-strand conformational polymorphism (SSCP) analyses. These isoforms are termed "human NF2 transcript isoform I" and "human NF2 transcript isoform II," herein. Human NF2 transcript isoform I is depicted in FIGS. 1A–1C (SEQ ID NO:3). The full-length sequence of human NF2 transcript isoform I includes 1785 base pairs and encodes a protein of 595 amino acids, variously known as the merlin protein (Trofatter et al. (1993) *Cell* 72:791–800) and schwannomin (Rouleau et al. (1993) *Nature* 363:515–521). The protein was originally believed to consist of 587 amino acids (as reported in Trofatter et al. (1993) *Cell* 72:791–800). The corrected NF2 cDNA sequence has been assigned GenBank Accession No. L11353.

Human transcript isoform II carries a 45 bp insertion at nucleotide 1737, which encodes 11 amino acids and a premature termination codon, thus resulting in a variable C-terminus. The transcript encodes a putative protein of 590 amino acids. (See, FIGS. 6 and 7A–7D) (SEQ ID NO:9).

As shown in the examples, these isoforms are expressed in multiple tissue and tumor types. Both of the human isoforms were shown to be present in several normal tissues, including heart, brain, lung, liver, skeletal muscle, kidney, pancreas and placenta, as well as in total RNA extracted from the eighth cranial nerve (the tissue from which vestibular schwannomas derive), adrenal gland and cerebellum. Human transcript isoform II appears to be present in much lower levels in the adrenal gland and the eighth cranial nerve as compared to isoform I. However, human transcript isoform II is the predominant species in RNA from the cerebellum. This novel isoform was also detected in an NF2 cDNA clone isolated from a fetal brain cDNA library. The two isoforms were also found to be present in cancerous tumors, including in glioblastoma, meningioma, and acoustic neuroma. Human transcript isoform II was also found to be expressed in three colon carcinomas, with almost complete absence of isoform I.

Mutations affecting both of the human transcript isoforms described above were detected in multiple tumor types, including sporadic vestibular schwannomas, as well as in malignant melanoma and breast carcinoma, both tumor types of which are unrelated to NF2 disease, suggesting that these NF2 transcript isoforms are generally important in tumorigenesis.

Several mouse NF2 transcript isoforms have also been identified. Exemplary transcript isoforms, termed "mouse transcript isoform I," "mouse transcript isoform II" and "mouse transcript isoform III," are described herein. The full-length coding cDNA sequence of mouse transcript isoform I is 1788 bp in length, shares 90% sequence identity with the human NF2 cDNA, and encodes a putative protein of 596 amino acids, sharing 98% homology with the protein encoded by human transcript isoform I (see FIGS. 1A–1C (SEQ ID NO:1 and 3). Murine transcript isoforms II and III carry a 45 bp and 16 bp insertion, respectively, at nucleotide 1740 at the 3'-end; both insertions introduce premature termination codons (see FIGS. 4A (SEQ ID NO:4) and 4B (SEQ ID NO:6)). Transcript isoforms II and III predict proteins of 591 and 584 amino acids, respectively (FIGS. 2 (SEQ ID NO:5) and 3 (SEQ ID NO:7), respectively), with altered C-termini of more hydrophilic character as compared to isoform I. Northern blot analysis and PCR analysis indicate that the mouse NF2 gene is widely expressed in different tissue types and that alternative transcripts are tissue variantly expressed. In particular, mouse transcript isoform II was shown to be more abundantly expressed than isoform I in brain, heart, liver and lung. In contrast, isoform I was the predominantly expressed species in spleen and testis. Weak but detectable expression of isoform III was observed only in spleen and testis. Although originally identified as an isolated cDNA clone from a mouse brain cDNA library, no amplification of isoform III was detected in mouse brain RNA.

Mouse transcript isoform I was obtained from a mouse brain cDNA library screened using a PCR fragment representing nearly the entire coding region of the human NF2 cDNA as a probe. Transcript isoform II was identified by reverse transcription-PCR (RT-PCR) analysis of mouse brain RNA using oligonucleotide primers flanking the insertion site at nucleotide 1740. Transcript isoform III was identified in a cDNA clone (clone λZ8).

The above-described human and mouse NF2 transcript isoforms, as well as NF2 transcript isoforms from other species, tissues and tumor types, can be conveniently identified using such techniques as PCR, SSCP, RNase cleavage, combinations of these methods, or any other techniques which are known to detect mutations at the nucleic acid level. PCR employs short oligonucleotide primers which match opposite ends of a desired sequence. The sequence between the primers need not be known. The initial template can be either RNA or DNA. If RNA is used, it is first reverse transcribed to cDNA. The cDNA is then denatured, using well known techniques, such as heat, and appropriate oligonucleotide primers are added in molar excess. Polymerization is accomplished using polymerase in the presence of deoxynucleotide triphosphates or nucleotide analogs. The resulting product includes the respective primers at their 5'-termini, covalently linked to the newly synthesized complements of the original strands. The replicated molecule is again denatured, hybridized with primers, and so on, until the product is sufficiently amplified. PCR methods are described in e.g., U.S. Pat. Nos. 4,965,188; 4,800,159; 4,683,202; 4,683,195; incorporated herein by reference in their entireties.

SSCP, a method also well known in the art, makes use of differential electrophoretic mobilities resulting from conformational differences found between two short single-stranded DNA molecules. RNase cleavage similarly detects mutations at the nucleic acid level. For detecting mutations using RNase cleavage, DNA containing the sequence to be analyzed, is cloned into a vector that encodes a phage RNA polymerase. Radioactive RNA can be synthesized for use as a probe. The genomic DNA is digested using a restriction endonuclease that cleaves at sites outside of the region of interest, and this DNA is hybridized with the RNA probe. If the DNA sample contains the wild-type sequence, a perfect RNA-DNA hybrid is formed. If the DNA includes one or more mutations, the RNA-DNA hybrid contains a mismatch. At the site of the mismatch, the RNA is single-stranded. Since RNase A only cuts single-stranded RNA molecules, when the hybrid molecule is treated with this enzyme, the strand with a mismatch will be cleaved at the site and cleavage can be detected using an analytical gel. See, e.g., Myers et al. (1985) *Science* 230:1242–1246; Gibbs, R. and Caskey, C. T. (1987) *Science* 236:303–305.

Due to the conserved nature of the NF2 gene isoforms, the sequences disclosed herein can be used to design oligonucleotide probes to detect the presence of these or similar genes in other species, tissues and tumor types. In particular, genomic and cDNA libraries, derived from the desired tissue, can be prepared using techniques well known in the art. Oligonucleotide probes which contain the codons for a portion of the determined sequence can be prepared and used to screen the libraries for these and homologous NF2 genes. The basic strategies for preparing oligonucleotide probes and DNA libraries, as well as their screening by nucleic acid hybridization, are well known to those of ordinary skill in the art. See, e.g., *DNA Cloning:* Vol. I, supra; *Nucleic Acid Hybridization,* supra; *Oligonucleotide Synthesis,* supra; Sambrook et al., supra. Once a clone from the screened library has been identified by positive hybridization, it can be confirmed by restriction enzyme analysis and DNA sequencing that the particular library insert indeed contains an NF2 gene and the gene can be isolated. See, e.g., Sambrook et al., supra.

If desired, the DNA sequence can be prepared synthetically using techniques known in the art. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been synthesized or isolated, they can be cloned into any suitable vector for expression. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning:* Vols. I & II, supra; Sambrook et al., supra; B. Perbal, supra. Insect cell expression systems, such as baculovirus systems, can also be used and are known to those of skill in the art and described in, e.g., Summers and Smith, *Texas Agricultural Experiment Station Bulletin* No. 1555 (1987). Materials and methods for baculovirus/insect cell expression systems are commercially available in kit form from, inter alia, Invitrogen, San Diego Calif. ("MaxBac" kit).

The gene can be placed under the control of a promoter, ribosome binding site (for bacterial expression) and, optionally, an operator (collectively referred to herein as "control" elements), so that the DNA sequence encoding the desired NF2 protein is transcribed into RNA in the host cell transformed by a vector containing this expression construction. The coding sequence may or may not contain a signal peptide or leader sequence. Heterologous leader sequences can be added to the coding sequence which cause the secretion of the expressed polypeptide from the host organism. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the NF2 protein of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning,* Vols. I and II, supra; *Nucleic Acid Hybridization,* supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis,* and Streptococcus spp., will find use with the present expression constructs. Yeast hosts useful in the present invention include inter alia, *Saccharomyces cerevisiae, Candida albicans, Candida maltosa, Hansenula*

*polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda,* and *Trichoplusia ni*. The proteins may also be expressed in Trypanosomes.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art. Once purified, the amino acid sequences of the proteins can be determined, i.e., by repetitive cycles of Edman degradation, followed by amino acid analysis by HPLC. Other methods of amino acid sequencing are also known in the art.

The NF2-encoded proteins of the present invention may also be produced by chemical synthesis such as solid phase peptide synthesis, using known amino acid sequences or amino acid sequences derived from the DNA sequence of the genes of interest. Such methods are known to those skilled in the art.

Once produced, the NF2 proteins can be used in pharmaceutical compositions to ameliorate NF2 disease or tumors associated with NF2 mutations. The NF2-encoded proteins of the present invention can be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular cancer type targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., *Remington's Pharmaceutical Sciences,* Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration, to the tumor in question, will also find use with the present invention.

Therapeutically effective doses will be easily determined by one of skill in the art and will depend on the severity and course of the disease, the patient's health and response to treatment, and the judgment of the treating physician.

An alternative route of administration involves gene therapy. Thus, the NF2 transcript isoforms (and accompanying regulatory elements) can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al. *Science* (1990) 247:1465–1468). Liposome-mediated gene transfer can also be accomplished using known methods. See, e.g., Hazinski et al. *Am. J. Respir. Cell Mol. Biol.* (1991) 4:206–209; Brigham et al. *Am. J. Med. Sci.* (1989) 298:278–281; Canonico et al. *Clin. Res.* (1991) 39:219A; and Nabel et al. *Science* (1990) 249:1285–1288. Targeting agents, such as antibodies directed against surface antigens expressed on specific cell types, can be covalently conjugated to the liposomal surface so that the nucleic acid can be delivered to specific tissues and tumor types.

The NF2-encoded proteins of the present invention or their fragments can also be used to produce antibodies, both polyclonal and monoclonal. If polyclonal antibodies are desired, a selected mammal, (e.g., mouse, rabbit, goat, horse, pig etc.) is immunized with an antigen of the present invention, or its fragment, or a mutated antigen. Serum from the immunized animal is collected and treated according to known procedures. If serum containing polyclonal antibodies is used, the polyclonal antibodies can be purified by a variety of methods, such as by immunoaffinity chromatography, using known procedures.

Monoclonal antibodies to the NF2 proteins, and to the fragments thereof, can also be readily produced by one skilled in the art using, e.g., hybridoma technology. The general methodology for making monoclonal antibodies by using hybridoma technology is well known. For example, immortal antibody-producing cell lines can be created by cell fusion, as well as by other techniques such as direct transformation of B lymphocytes with oncogenic DNA, or transfection with Epstein-Barr virus. See, e.g., M. Schreier et al. *Hybridoma Techniques* (1980); Hammerling et al. *Monoclonal Antibodies and T-cell Hybridomas* (1981); Kennett et al. *Monoclonal Antibodies* (1980); U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the NF2 proteins can be screened for various properties; i.e., for isotype, epitope, affinity, etc.

The antibodies generated against the NF2-encoded proteins can be used in standard immunoassays, as diagnostic reagents, to screen tissues and/or tumors for the presence or absence of the proteins, or for the presence or absence of aberrant NF2 proteins, allowing for identification of individuals with NF2 disease, as well for the identification of carriers of the disease and the determination of individuals likely to develop NF2 disease. For example, the presence of NF2 proteins can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the NF2 proteins and the antibodies described above.

Solid supports can be used in the assays such as nitrocellulose, in membrane or microtiter well form; polyvinylchloride, in sheets or microtiter wells; polystyrene latex, in beads or microtiter plates; polyvinylidine fluoride; diazotized paper; nylon membranes; activated beads, and the like. Typically, the solid support is first reacted with the biological sample, washed and then the antibodies are applied. If a sandwich type format is desired, such as a sandwich ELISA assay, a commercially available anti-immunoglobulin (i.e. anti-rabbit immunoglobulin) conjugated to a detectable label, such as horseradish peroxidase, alkaline phosphatase or urease, can be added. An appropriate substrate is then used to develop a color reaction.

Alternatively, a "two antibody sandwich" assay can be used to detect both aberrant and wild-type NF2 proteins. In this technique, the solid support is reacted first with one or more of the antibodies, washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the NF2 proteins and antibodies thereto form complexes under precipitating conditions. The precipitated complexes can then be separated from the test sample, for example, by centrifugation. The reaction mixture can be analyzed to determine the presence or absence of antibody-NF2 complexes using any of a number of standard methods, such as those immunodiagnostic methods described above.

The NF2 proteins and antibodies can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Experimental Methods

Northern analysis. A Northern blot (Clontech Laboratories, Inc.) containing 2 µg of poly A+ RNA from eight human tissues, or multiple murine tissues, was hybridized to a [$\alpha$-$^{32}$P] dCTP-labeled probe generated by reverse transcription-PCR amplification (RT-PCR) of the entire NF2 coding region. Filter hybridization was performed at 68° C. for 3 h using the Quickhyb™ solution (Stratagene, La Jolla, Calif.), followed by two washes with 2×standard saline citrate (SSC) (1×SSC=0.15 M NaCl, 0.015 M sodium citrate)/0.1% sodium dodecyl sulfate (SDS) for 15 min at room temperature, and one wash with 0.1×SSC/0.1% SDS for 15 min at 54° C.

Reverse Transcription-PCR (RT-PCR) Amplification. Total RNA was extracted from frozen human tumor specimens or murine tissues by lysis in guanidium thiocyanate and extraction with phenol-chloroform as described in Chomczynski et al. (1987) *Anal. Biochem.* 162:156–158. Total RNA was denatured by heating to 70° C. for 10 min in 13 µl of DEPC-treated water. After chilling on ice for 2 min, single-stranded cDNA was synthesized by incubating the denatured RNA in 20 µl 20 mM Tris-HCl (pH 8.4), 50 mM KCl, 2.5 mM MgCl$_2$, 100 ng/µl bovine serum albumin (BSA), 500 µM dNTP, 10 mM dithiothreitol (DTT), 12 ng/µl of primer 3m3 or 3m6 (tumor specimen extracts) or the specific primer 3AS1 (complementary to the 3' end of the mouse NF2 mRNA) and 5m9 (murine tissue extracts), and 200 U of SuperScript™ (Gibco BRL) reverse transcriptase for 10 min at room temperature followed by 60 min at 42° C. The reaction was terminated by heating to 95° C. for 2 min and quenching on ice. A first amplification by polymerase chain reaction (PCR) was performed using 2 µl of the reverse-transcribed product in a final volume of 100 µl such that final concentrations were 20 mM Tris-HCl (pH 8.2), 10 mM KCl, 6 mM (NH$_4$)$_2$SO$_4$ 1,5 mM MgCl$_2$, 0.1% Triton X-100, 2.5 U Pfu DNA polymerase (Stratagene), 200 µM each deoxynucleoside triphosphate, and 0.3 pmole/µl of primers 5m1 and 3m3 (for the 3m3-primed first strand cDNA) or 5m4 and 3m6 (for the 3m6-primed product) (tumor specimen extracts) or 3AS1 and 5AS1 (murine tissue extracts). Nested PCR amplifications were performed using 1 µl of first amplification product in a final volume of 100 µl (tumor specimen extracts) or 50 µl (murine tissue extracts) of solution containing 10 mM Tris-HCl (pH 8.3), 50 mM KCl, 1.5 mM MgCl$_2$, 0.001% (tumor specimen extracts) or 0.01% (murine tissue extracts) (w/v) gelatin, 200 µM (tumor specimen extracts) or 250 µM (murine tissue extracts) each deoxynucleoside triphosphate, 0.3 pmole/µl of appropriate primers, and 2.5 U Taq polymerase (Boehringer Mannheim). 30–32 cycles of amplification were performed in a Gene-Amp 9600 machine (Perkin Elmer), with denaturation at 94° C. for 15 sec, annealing at 58° C. for 15 sec, and elongation at 72° C. for 1 min and 15 sec. Final extension was at 72° C. for 3 min (murine tissue extracts). The oligonucleotide primers used in reverse transcription and PCR amplification were as follows:

5m1: 5'-CATGGCCGGGCCATCGCTTCC-3' (SEQ ID NO:11);

3m1: 5'-CCTGAACCAGCTCCTCTTCAGC-3' (SEQ ID NO:12);

5m2: 5'-TCAAAGGAAGAACCAGTCACC-3' (SEQ ID NO:13);

3m2: 5'-TCAGCTTCATCCCTGGCTCG-3' (SEQ ID NO:14);

3m3: 5'-GGAGAGAATTACTGCTTGGT AC-3' (SEQ ID NO:15);

3m3: 5'-CATAAATAGATCATGGTTCCCGAT-3' (SEQ ID NO:16);

5m4: 5'-CCTCAAAGCTTCGTGTTAATAAGC-3' (SEQ ID NO:17);

3m4: 5'-TTCCTGCTCAGCCTCTGCGGC-3' (SEQ ID NO:18);

5m5: 5'-GGAGGCAAAACTTCTGGCCCAG-3' (SEQ ID NO:19);

3m5: 5'-GACAGGCTGTCACCAATGAGG-3+ (SEQ ID NO:20);

5m6: 5'-CAATTCCAGCACCGTTGCCTCC-3' (SEQ ID NO:21);

3m6: 5'-GGGTGGCTGGGTCACCTGCT-3' (SEQ ID NO:22);

5m9: 5'-GTGGAGTACATGGAGAA-3+ (SEQ ID NO:23); (extending from nucleotide 1576 with respect to the full length mouse NF2 cDNA):

3AS1: 5'-TCTTCAAAGAAGGCCACTCG-3' (SEQ ID NO:24);

5AS1: 5'-ACACAGCGAGAGCTCAGACAGA-3' (SEQ ID NO:25); (extending from nucleotide 1684 with respect to the full length mouse NF2 cDNA).

Tumor samples listed in Table 1 were amplified by RNA PCR using the following oligonucleotide primer sets:

AN54: 5m1-3m1; AN10, AN13, AN72, AN26, 95540: 5m2-3m2; AN94, 86336, 90021: 5m3-3m3; AN825, 94771: 5m4-3m4; 86-20: 5m4-3m5; AN11, 87506, 95783: 5m5-3m6.

Single Strand Conformational Polymorphism (SSCP) Analysis. Nested PCR amplifications were performed for SSCP analysis using the following reaction mixture (final volume 50 µl): 1 µl of PCR-amplified template, 10 mM Tris-HCl (pH 8.3), 50 mM KCl, 1.5 mM $MgCl_2$, 0.001% (w/v) gelatin, 200 µM of each dCTP, dGTP, dTTP, 20 µM dATP, 0.1 µl of [$\alpha$-$^{33}$P] dATP (3000 Ci/mmol) (Du Pont NEN), 0.3 pmole/µl of appropriate primers, and 1.25 U Taq polymerase. Following amplification, PCR products were diluted (1:10) with 0.1% SDS/10 mM EDTA. A 5 µl sample of the diluted reaction was then mixed with 6 µl of gel loading dye (U.S. Biochemical Corporation). Samples were heat denatured at 94° C. for 2 min, chilled on ice, and 3 µl loaded onto a 0.5X MDE gel (J. T. Baker, Inc.). Gels were electrophoresed at 8 watts constant power for 14 hours at room temperature using 0.6X Tris borate EDTA (TBE) buffer. After electrophoresis, gels were transferred to blotting paper, dried and subjected to autoradiography.

Genomic DNA PCR analysis. Genomic DNA extracted from the patients' blood was analyzed by PCR using oligonucleotide primers that flank the exon-intron junctions of the NF2 gene.

Sequence analysis. Individual bands were carefully excised from agarose gels or from dried SSCP gels, placed into 100 µl of deionized water, and the DNA allowed to elute for 4–6 hr at room temperature with gentle shaking. 10 µl of eluted DNA was reamplified using appropriate primers as described above. Amplified products were subcloned into the plasmid vector pCR™ II (Invitrogen Corp.), and inserts were sequenced using double-stranded recombinant plasmids as template for the dideoxy chain termination method as described in Sanger et al. (1977) *Proc. Natl. Acad. Sci. USA* 74:5463–5467. Reaction products were electrophoresed on 6% polyacrylamide, 8 M urea, 0.1 M Tris-borate (pH 8.3), 2 mM EDTA gels. Some of the clones were sequenced by dideoxy termination chemistry using an Applied Biosystems 373-A automated DNA sequencer. Double strand sequencing of three clones was performed for each mutant sample. Sequence data was analyzed using the MacVector™ 4.1 software (International Biotechnologies, Inc.).

Cloning of Mouse NF2 cDNAs. A mouse brain oligo (dT) and random-primed cDNA library in λZAPII (Stratagene) was screened by plaque hybridization to $10^6$ filter-immobilized cDNA phage clones at a density of $5 \times 10^4$ plaque forming units (pfu)/150-mm filter. A $^{32}$P-labeled (Feinberg et al. (1983) *Anal. Biochem.* 132:266–267) PCR fragment representing nearly the entire coding region of the human NF2 cDNA (nucleotides 219 to 2031, as numbered in Trofatter et al. (1993) *Cell* 72:791–800) was used as a probe.

Prehybridization was performed at 65° C. for 3 hr in 4×standard sodium phosphate EDTA (SSPE) (1×SSPE=0.15 M NaCl, 0.010 M $NaH_2PO_4.H_2O$, 0.001 M EDTA-$Na_2$, pH 7.4), 6% polyethylene glycol 8000, 0.5% sodium dodecyl sulfate, 2×Denhardt's solution and 100 mg/ml denatured sheared salmon sperm DNA. Hybridization was then carried out at 65° C. in the same solution containing radiolabeled probe. Washes were performed under high stringency. Filters were exposed overnight to Kodak X-AR films at −80° C. with intensifying screens. After 3 rounds of screening, cDNAs were rescued as pBluescript SK-phagemids (Stratogene) by in vivo excision using the R408 helper phage.

The nucleotide sequences of recombinant clones of mouse NF2 cDNAs were determined by the dideoxy chain termination method, as described above, using Sequenase version 2.0 (US Biochemical, Cleveland, Ohio). Both strands were sequenced and analyzed using MacVector™ 4.1 software.

EXAMPLE I

Cloning of Murine NF2 Transcript Isoform I Gene

In order to clone and characterize the mouse NF2 gene, a murine NF2 cDNA homolog was isolated as follows. A mouse brain cDNA library in λZAPII was screened with the $^{32}$P-labeled DNA probe spanning nearly the entire human NF2 gene coding region. Twelve positive plaques were analyzed in more detail and helper phage-rescued phagemids (pBluescript) tested for insert size after the third round of screening. Four clones with inserts of 2.0 kb, 0.8 kb, 3.5 kb and 2.0 kb were overlapping clones that cover the entire coding region of the mouse NF2 gene. The complete nucleotide and deduced amino acid sequences of the mouse NF2 cDNA, as derived from sequence analysis of both strands of these clones, are shown in FIGS. 1A–1C (SEQ ID NO:1 and 2). The coding region consists of 1788 nucleotides, encoding a predicted protein of 596 amino acids with a calculated molecular mass of 69–70 kDa, as compared to 595 amino acids for the human protein. The one residue difference is based on the presence of a three base insertion (CCC) at nucleotide 1710, introducing a proline at this site. Sequence analysis of all isolated cDNA clones, and RT-PCR products derived from mouse brain RNA, revealed the presence of this proline, indicating that this residue is specific to the predicted mouse merlin protein. This was confirmed by sequencing of genomic DNA, which revealed that the 3 bp insertion does not represent a distinct exon in the mouse.

The overall homology of mouse and human NF2 cDNAs is 90% at the nucleotide level (a total of 172 bp substitutions) and 98% at the deduced amino acid level (a total of 10 substitutions, 7 of which constitute conservative changes and 2 of which represent semiconservative changes). These substitutions are clustered toward the C-terminus of the predicted protein.

EXAMPLE II

Identification of Transcript Isoforms in Murine Brain

Alternative transcript isoforms of the mouse NF2 gene were identified in several of the cDNA clones described in Example I. Clone λZ8 showed an insertion of 16 bp at nucleotide 1740 (see FIG. 4B (SEQ ID NO:6)). In order to determine whether the 45 bp insertion in the alternative transcript isoform detected in the human NF2 gene (see Example VII) was also expressed in murine tissue, RT-PCR was performed on murine brain RNA using oligonucleotide primers flanking the insertion site at nucleotide 1740. Two PCR products were identified by agarose gel electrophoresis. Sequencing of the largest PCR product revealed the presence of a 45 bp insertion at nucleotide 1740, which was identical in sequence to that described for the human NF2 transcript except for one bp difference (FIG. 4A (SEQ ID NO:4), see arrow).

In concordance with the numbering system used for the human transcript variants, the mouse transcript with the 45 bp insertion was designated as isoform II, while the mouse transcript with the 16 bp insertion was designated as isoform III. The 45 bp insertion in transcript isoform II encoded 11 amino acids in frame and introduced a premature stop codon, predicting a protein of 591 amino acids. The 16 bp insertion in transcript isoform III encoded 4 amino acids in frame before introducing a premature stop codon, and thus encoded a putative protein of 584 amino acids.

EXAMPLE III

Modes of Splicing Giving Rise to Murine Transcript Isoforms

In order to determine the mechanisms by which the murine NF2 transcript isoforms arise, exon-intron boundary information was obtained as follows. Mouse genomic DNA harboring the 3' end of the mouse NF2 gene was analyzed. PCR was used to amplify mouse genomic DNA across the region from nucleotide 1684 (primer 5AS1) and the 45 bp sequence present in isoform II (antisense primer II-3': 5'-GAGGACTCAAATGCAGATAGGTCT-3'(SEQ ID NO:26)). The size of the amplified DNA fragment was about 1.5 kb. The fragment was subcloned and subjected to sequence analysis. Sequence analysis was performed with primers 5AS1 and II-3' in order to determine the exon-intron boundaries.

Figure 5:
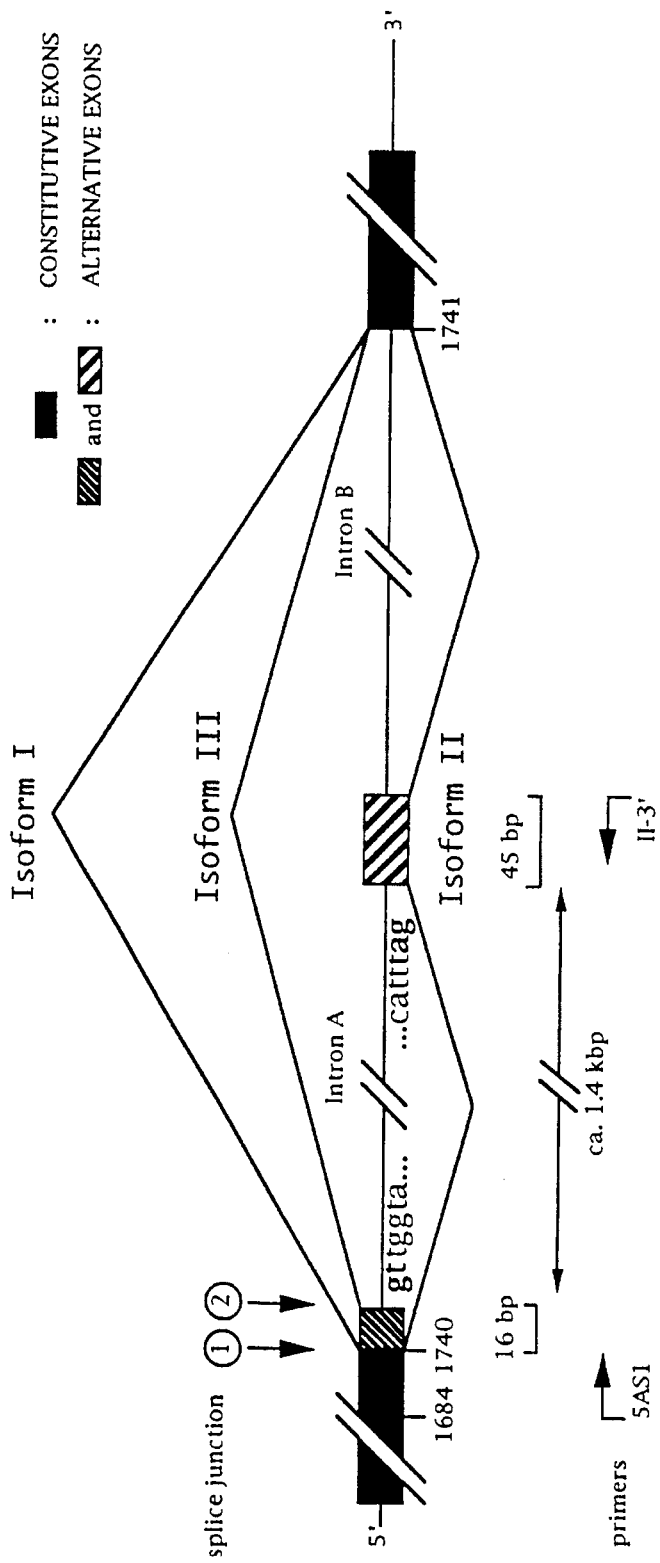
FIG. 5 depicts the mouse NF2 gene structure in the region of alternative splicing. Exons are represented by boxes, and flanking introns (A and B) by lines. Intronic sequences at the relevant splice junctions are indicated.
Figure 6:
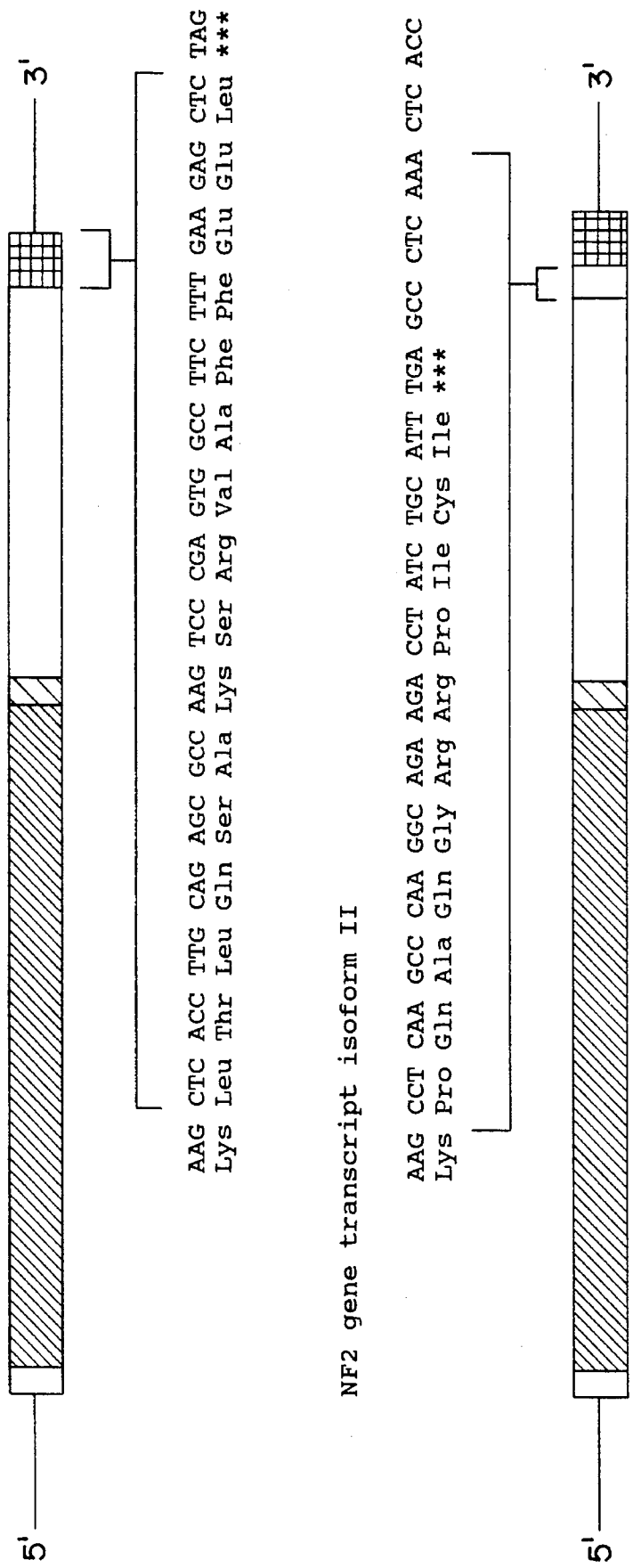
FIG. 6 shows a comparison of the partial nucleotide (SEQ ID NO:8) and predicted amino acid sequence (SEQ ID NO:3, amino acids 580 to 596) at the 3' end of human NF2 transcript isoform I and the partial nucleotide (SEQ ID NO:9, nucleotides 1954 to 2007) and predicted amino acid sequence (SEQ ID NO:10, amino acids 580 to 591) at the 3' end of human isoform II. The checkered box in isoform I indicates the nucleotide sequence encoding a variable C terminus of 16 amino acids. The black box in isoform II indicates the 45 bp insertion, and the predicted amino acid sequence, that gives rise to isoform II. Coding regions with high (densely hatched box) and partial (hatched box) homology to moesin, ezrin and radixin, are shown.

Two distinct modes of splicing appeared to be involved in the generation of isoforms I, II, and III. FIG. 5 shows a schematic description of the mouse NF2 gene structure in this region, as determined by sequence analysis of mouse genomic DNA. In genomic DNA, the 16 bp insertion sequence present in transcript isoform III is contiguous with and represents an extension of the upstream exon; no distinct intron separates the 5' constitutive exon from the alternative exon of 16 bp. In contrast, sequencing beyond the 16 nucleotides revealed an intronic sequence. Similarly, sequencing with primer II-3' revealed intronic sequences at the 5'-boundary of the 45 bp sequence found in isoform II cDNA. Thus, the 45 bp sequence represents a distinct exon and is separated from the 3' end of the 16 bp insertion sequence by about 1.4 kb. The different splicing pathways are shown by the diagonal lines.

The mechanisms of the different splicing pathways appear to include:

(a) alternative 5'-donor sites: transcript isoforms I and II are generated by usage of an alternative 5'-donor site within a particular exon, resulting in excision of an intron of different length and a reduction in exon size of 16 bp, as compared to that in isoform III.

(b) a casette exon: transcript isoform II is generated as a variant of isoform I by inclusion of a distinct alternative exon of 45 bp in length.

EXAMPLE IV

Detection of NF2 Transcript Isoforms in Different Mouse Tissues by RT-PCR Amplification The presence of NF2 transcript isoforms in different mouse tissues was detected by performing reverse transcriptase-PCR analysis of various mouse tissue RNAs using primers 5AS1 and 3AS1 flanking the alternative splice site at nucleotide 1740. The identify of all three PCR-amplified DNA fragments was confirmed by subcloning and sequencing. A variable pattern of expression was observed for the various transcript isoforms. Isoform II was more abundantly expressed than isoform I in tissues such as brain, heart, liver and lung. In contrast, isoform I was the predominantly expressed species in spleen and testis. Weak but detectable expression of isoform III was observed only in spleen and testis. Although originally identified as an isolated cDNA clone from a mouse brain cDNA library, no amplification of isoform III was detected in mouse brain.

EXAMPLE V

Detection of NF2 Transcript Isoforms in Different Mouse Tissues by Northern Blot Analysis In order to conduct a further analysis of the expression of NF2 in various mouse tissues, Northern blot analysis was performed. The mouse NF2 gene was found to be widely expressed in tissues such as heart, brain, spleen, lung, liver, skeletal muscle, kidney and testis. A single predominantly hybridizing species of about 6 kb was detected in all tissues, with highest expression in heart, brain and testis. These results indicate that the expression of the mouse NF2 gene is clearly not restricted to the central nervous system.

EXAMPLE VI

Detection of an NF2 Gene in Other Species

In order to determine whether the NF2 gene is conserved in species other than mouse, Southern blots were performed using a human NF2 cDNA probe. Filter-immobilized DNA (8 μg/lane) from differenect species was hybridized with a $^{32}$P-labeled human NF2 cDNA probe. Blots were exposed to Kodak X-AR films at −80° C. with intensifying screens from 2 hr to 3 days. Strong hybridization was detected to DNA from species such as rat, dog, cow, rabbit and chicken. These results indicate that the NF2 gene is highly conserved during evolution.

EXAMPLE VII

Expression of the NF2 Gene in Human Tissue

In order to evaluate the pattern of expression of the NF2 gene in humans, Northern blot analyses were performed using poly(A)$^+$ RNA isolated from various human tissues. Two major transcripts of approximately 2.6 kb and 7 kb, together with a weakly hybridizing species of 4.4 kb, were detected in heart, brain, lung, liver, skeletal muscle, kidney, pancreas, and placenta (a very faint signal was observed in overexposed Northern blots). PCR analysis also revealed the presence of NF2 gene transcripts in total RNA extracted from the eighth cranial nerve, adrenal gland and cerebellum, indicating that expression of the NF2 gene is not restricted to the CNS but occurs in a wide variety of human tissues.

EXAMPLE VIII

Alternative Splicing at the 3' End of the Human NF2 Gene Transcript

PCR analysis of the NF2 gene transcript using primers 5m6 and 3m6 revealed the presence of two distinct products of 350 bp and 395 bp in different human tissues including the eighth cranial nerve (the tissue from which vestibular schwannomas derive). Analysis of one of these transcripts confirmed a sequence identical to merlin, reported previously (Trofatter et al. (1993) *Cell* 72:791–800; Rouleau et al. (1993) *Nature* 363:515–521), whereas the product with higher molecular weight revealed a 45 bp insertion at nucleotide 1737, encoding eleven amino acids and a premature termination of the reading frame (FIGS. 6 and 7A–7D (SEQ ID NO:9)). This insertion was also detected in an NF2 cDNA clone isolated from a fetal brain cDNA library. The novel isoform of the NF2 gene transcript, which presumably arises by alternative splicing, encodes a 590 amino acid protein with a modified C terminus. Therefore, the predicted C terminus of both NF2 gene products would differ by a total of sixteen amino acids. The novel NF2 gene alternative splice variant has been designated isoform II, and the original NF2 gene transcript published previously (Trofatter et al. (1993) *Cell* 72:791–800; Rouleau et al. (1993) *Nature* 363:515–521) as isoform I.

EXAMPLE IX

Identification of NF2 Isoforms in Different Human Tissues and Tumor Types

The location and predicted amino acid sequence of the alternative splice variant were found to be completely conserved in the mouse (see Example II). In addition, RNA PCR analysis showed marked differences in the relative abundances of both NF2 gene transcript isoforms in a number of tissues and tumor types. Whereas isoform II showed very low relative expression levels in adrenal gland and the eighth cranial nerve, isoform II of the NF2 gene transcript was the predominant species in RNA from cerebellum. By contrast, both isoforms showed similar expression levels in kidney. Similarly, differences in the relative expression levels of isoform I and II transcripts were observed in different tumor types. In particular, isoform II was expressed predominantly in three colon carcinomas analyzed with almost complete absence of isoform I.

RNA PCR analysis of one vestibular schwannoma (AN11) using oligonucleotide primers that flank the alternative splice site near the 3' end of the NF2 gene transcript (5m6 and 3m6) showed a unique fragment of reduced size (187-bp) in comparison with the products derived from isoforms I and II (350 bp and 395 bp, respectively) in normal tissue. Sequencing of the aberrant product confirmed a 163 bp deletion (nucleotides 1575–1737) that included the alternative splice site at nucleotide 1737 (Table 1). This deletion near the 3' end of the NF2 gene transcript would result in the removal of fifty four amino acids, including the C-terminal end of isoform II of merlin, and would introduce a frameshift in the reading frame of isoform I.

EXAMPLE X

NF2 Gene Mutations in Vestibular Schwannomas

To investigate the presence of mutations within the NF2 gene coding region in tumors typically associated with NF2, a PCR/SSCP analysis was performed in RNA from vestibular schwannomas.

A total of twelve sporadic and three NF2-associated vestibular schwannomas were screened (Table 1). A preliminary analysis of the PCR-amplified products by agarose gel electrophoresis revealed fragments of reduced size in five tumor samples, including tumors AN10 and AN825, wherein deletions in the NF2 gene transcript were evidenced by the presence of fragments of 269 bp and 251 bp, respectively. SSCP analysis of the remaining cases detected a variant electrophoretic pattern in three additional tumors, including AN13. Cloning and double strand sequencing of the aberrant RNA PCR fragments demonstrated the presence of mutations in each of the tumors showing products of altered size. As summarized in Table 1, mutations within the NF2 coding region were detected in two of three hereditary and in six of twelve sporadic vestibular schwannomas. One tumor (AN11) carried a NF2 cDNA deletion that introduced a frameshift resulting in premature termination of the reading frame within 56 bp of the deletion breakpoint (Table 1). The remaining seven vestibular schwannomas exhibited in-frame transcript deletions that would result in truncated proteins without altering the distal reading frame (Table 1). In some tumors (AN94, AN10, AN54, AN72 and AN825), in-frame cDNA deletions represented whole exons. The total absence of RNA PCR products derived from the normal allele was observed in five vestibular schwannomas (Table 1, tumors AN94, AN11, AN13, AN825, and AN72), consistent with the highly homogeneous nature of this tumor type which only exhibits minor contamination of non-neoplastic tissue.

The origin of the mutations was confirmed by screening lymphocyte genomic DNA from the patients. Mutation analysis of blood DNA from the patients bearing sporadic vestibular schwannomas AN94, AN10, AN11, AN54, AN72 and AN825 did not reveal any alterations in the NF2 gene, including the exon/intron junctions flanking the sequences deleted in the tumor cDNAs, thus confirming the somatic nature of these mutations (Table 1).

EXAMPLE XI

Analysis of Tumor Types Seemingly Unrelated to NF2

Since losses affecting chromosome 22q have been reported to occur in a variety of neoplasms, somatic mutations in the NF2 gene might be implicated not only in tumors typically associated with NF2 but also in seemingly unrelated cancers. Therefore, different tumor types from non-NF2 individuals, including breast and colon carcinomas, malignant melanomas, and pheochromocytomas, were screened for mutations within the NF2 gene coding region. Because NF2 is predominantly associated with tumors derived from the embryonic neural crest, a series of sporadic pheochromocytomas and melanomas, two tumor types that do not show a higher incidence in NF2 patients, were analyzed. Of three primary melanomas and seventeen melanoma metastases analyzed, sequencing of aberrant SSCP conformers demonstrated the presence of NF2 gene transcript mutations in six tumors. As shown in Table 1, in-frame deletions were detected in one primary skin melanoma (tumor 94771; superficial spreading type) and one melanoma metastasis (tumor 87506). The latter also exhibited an A to T transversion resulting in a nonconservative substitution of lysine to isoleucine (Table 1). The mutations detected in the remaining four melanoma metastases consisted of deletions of 1–143 bp that altered the reading frame generating premature stop codons (Table 1). A restriction enzyme map of the NF2 gene transcript indicated that the deletion observed in tumor 95540 would result in loss of a Bgl II site. Southern blot analysis of tumor DNA digested with Bgl II revealed an aberrant restriction pattern as compared to the control DNA, suggesting that the cDNA deletion described above is present at the genomic level. No apparent mutations in the NF2 cDNA were detected in five sporadic pheochromocytomas screened by RNA PCR/SSCP analysis.

Of fourteen primary breast carcinomas analyzed by RNA PCR/SSCP methods, one tumor showed a fragment of altered mobility. Sequence analysis of the altered-size PCR product demonstrated that this tumor, diagnosed as a poorly differentiated breast ductal carcinoma, carried a deletion of 211 bp that resulted in a frameshift, thereby introducing a premature termination codon within 74 bases of the deletion breakpoint (Table 1). Sequencing of this product also showed an A to T transversion at nucleotide 817 that would result in a substitution of isoleucine by phenylalanine (Table 1). This mutation was not detected in DNA from normal surrounding tissue, thus ruling out the possibility of a polymorphism. No apparent mutations in the NF2 gene coding region were detected in RNA samples extracted from twenty colon carcinomas.

EXAMPLE XII

Location of the NF2 Gene Transcript Deletions

Figure 8:
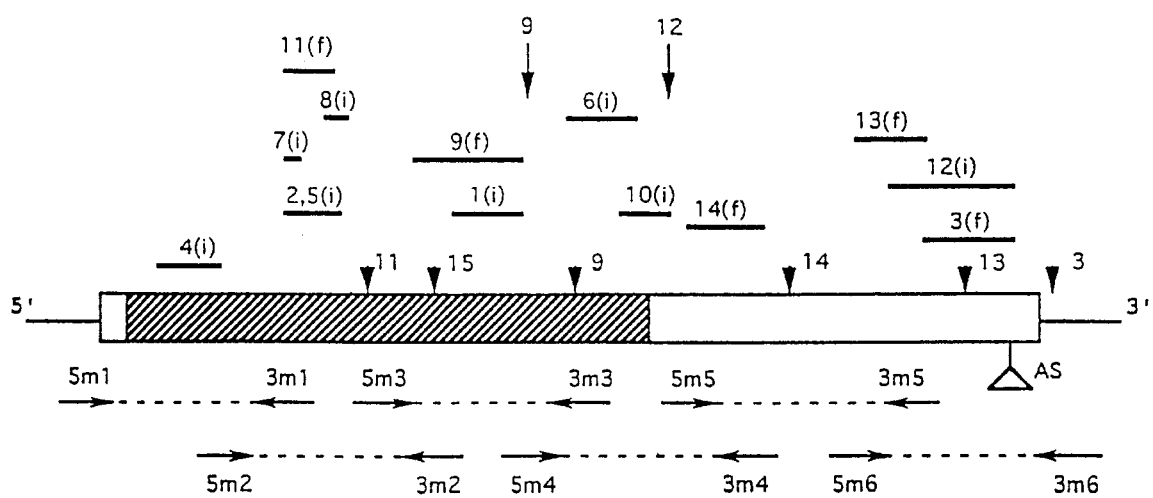
FIG. 8 is a schematic drawing showing the relative position of NF2 gene transcript mutations in different human tumor types. Numbers represent the tumors listed in Table 1 (1–15). Solid lines represent inframe (i) or frameshift (f) deletions. Vertical arrows indicate point mutations. The vertical arrow for sample No. 15 (melanoma 90021) represents a 1 bp deletion. The location of stop codons generated by frameshifts in the reading frame is indicated by solid vertical triangles. The coding region homologous to moesin, ezrin and radixin is represented by a hatched box. AS, alternative splice site. PCR oligonucleotide primers are represented by horizontal arrows.

An initial understanding of the potential functional significance of the different domains of the merlin protein may be gained from the location of the NF2 gene transcript deletions and their predicted effects on protein structure. Most of the alterations detected in this study (15 of 17 mutations; FIG. 8) are predicted to generate truncated proteins as the result of in-frame deletions or premature stop codons generated by reading frameshifts or point mutations. In most cases, these truncations would result in the removal of distal domains, including the α-helical and C-terminal regions, from the merlin protein. Although in some tumors the reading frame is preserved distal to the deletion breakpoint, it is likely that these dramatic alterations, which in some cases comprise whole exons, disrupt domains critical for merlin protein function. Evidence for function of the C terminus of merlin is provided by the frameshift deletion detected in vestibular schwannoma AN11 (Table 1), representing the most distal alteration. In this regard, the homozygous nature of this mutation, that predicts the removal of fifty four C-terminal amino acids, suggests that this region might be of critical importance for the putative tumor suppressor function of merlin.

TABLE 1

NF2 gene transcript mutations in human tumours.

| Tumour* | Histopathology** | Mutation† | Position†† | Effect¶ |
|---|---|---|---|---|
| 1) AN94 (s) | VS (S) | D135-bp | 676–810 | D (i) |
| 2) AN10 (s) | VS (S) | D84-bp | 364–447 | D (i) |
| 3) AN11 (s) | VS (S) | D163-bp | 1575–1737 | (f) > stop(1793) |
| 4) AN54 (s) | VS (S) | D126-bp | 115–240(113–238) | D (i) |
| 5) AN72 (s) | VS (S) | D84-bp | 364–447 | D (i) |
| 6) AN825 (s) | VS (S) | D114-bp | 886–999(888–1001) | D (i) |
| 7) AN13 (h) | VS (N/A) | D18-bp | 358–375 | D (i) |
| 8) AN26 (h) | VS (N/A) | D57-bp | 433–489 | D (i) |
| 9) 86336 | breast ductal CA | D211-bp | 600–810 | (f) > stop(884) |
|  |  | A > T | 817 | $Ile^{273}$ > Phe |
| 10) 94771 | melanoma | D87-bp | 1000–1086 (1003–1089) | D (i) |
| 11) 95540 | melanoma (m) | D85-bp | 361–445 | (f) > stop(518) |
| 12) 87506 | melanoma (m) | D228-bp | 1504–1731 (1501–1728) | D (i) |
|  |  | A > T | 1091 | $Lys^{364}$ > Ile |
| 13) 95783 | melanoma (m) | D125-bp | 1447–1571 | (f) > stop(1646) |
| 14) 86-20 | melanoma (m) | D143-bp | 1123–1265 | (f) > stop(1323) |
| 15) 90021 | melanoma (m) | D1-bp | 616 | (f) > stop(623) |

*(s) sporadic and (h) hereditary tumour.
**VS, vestibular schwannoma; (S), somatic origin of the mutation; (N/A), no blood from the patient was available; CA, carcinoma; (m), metastasis.
†D, deletion. The number of base pairs deleted follows the corresponding symbol.
††Nucleotide position of the mutations relative to the NF2 gene initiation codon. Alternative nucleotide positions (due to the repeated nature of the deleted sequence boundaries) are given in parenthesis.
¶D, deletion; (i), in-frame; (f), frameshift. The number in parenthesis indicates the nucleotide position of the stop codon generated by the frameshift.

Thus, novel NF2 transcript isoforms and NF2-encoded proteins, as well as antibodies generated thereto, have been disclosed. Although preferred embodiments of the subject invention have been described in some detail, it is to be understood that obvious variations can be made without departing from the spirit and the scope of the invention as defined by the appended claims.

We claim:

1. An isolated NF2 transcript isoform, wherein the isoform is mouse NF2 transcript isoform I encoding a protein comprising the mouse amino acid sequence depicted in FIGS. 1A–1C (SEQ ID NO:2).

2. An isolated NF2 transcript isoform, wherein the isoform is mouse NF2 transcript isoform II encoding a protein comprising the amino acid sequence depicted in FIG. 2 (SEQ ID NO:5).

3. An isolated NF2 transcript isoform, wherein the isoform is mouse NF2 transcript isoform III encoding a protein comprising the amino acid sequence depicted in FIG. 3 (SEQ ID NO:7).

4. An isolated NF2 transcript isoform, wherein the isoform is human NF2 transcript isoform II encoding a protein comprising the amino acid sequence depicted in FIGS. 7A–7D (SEQ ID NO:10).

5. A nucleic acid construct comprising:

(a) the NF2 transcript isoform of claim 1; and (b) control sequences that are operably linked to said transcript isoform whereby said transcript isoform can be transcribed and translated in a host cell, and wherein at least one of said control sequences is heterologous to said transcript isoform.

6. A nucleic acid construct comprising:

(a) the nucleotide sequence of claim 2; and (b) control sequences that are operably linked to said transcript isoform whereby said transcript isoform can be transcribed and translated in a host cell, and wherein at least one of said control sequences is heterologous to said transcript isoform.

7. A nucleic acid construct comprising:

(a) the nucleotide sequence of claim 3; and (b) control sequences that are operably linked to said transcript isoform whereby said transcript isoform can be transcribed and translated in a host cell, and wherein at least one of said control sequences is heterologous to said transcript isoform.

8. A nucleic acid construct comprising:

(a) the nucleotide sequence of claim 4; and (b) control sequences that are operably linked to said transcript isoform whereby said transcript isoform can be transcribed and translated in a host cell, and wherein at least one of said control sequences is heterologous to said transcript isoform.

9. A host cell transformed by the nucleic acid construct of claim 5.

10. A host cell transformed by the nucleic acid construct of claim 6.

11. A host cell transformed by the nucleic acid construct of claim 7.

12. A host cell transformed by the nucleic acid construct of claim 8.

13. A method of producing a recombinant NF2-encoded protein comprising:

(a) providing a population of host cells according to claim 9; and (b) culturing said population of cells under conditions whereby the protein encoded by said nucleic acid construct is expressed, thereby producing said NF2-encoded protein.

14. A method of producing a recombinant NF2-encoded protein comprising:
   (a) providing a population of host cells according to claim 10; and
   (b) culturing said population of cells under conditions whereby the protein encoded by said nucleic acid construct is expressed, thereby producing said NF2-encoded protein.

15. A method of producing a recombinant NF2-encoded protein comprising:
   (a) providing a population of host cells according to claim 11; and
   (b) culturing said population of cells under conditions whereby the protein encoded by said nucleic acid construct is expressed, thereby producing said NF2-encoded protein.

16. A method of producing a recombinant NF2-encoded protein comprising:
   (a) providing a population of host cells according to claim 12; and
   (b) culturing said population of cells under conditions whereby the protein encoded by said nucleic acid construct is expressed, thereby producing said NF2-encoded protein.

* * * * *

UNITED STATES PATENT AND TRADEMARK OFFICE
CERTIFICATE OF CORRECTION

PATENT NO. : 5,578,462
DATED : November 26, 1996
INVENTOR(S) : SEIZINGER et al.

It is certified that error appears in the above-indentified patent and that said Letters Patent is hereby corrected as shown below:

Please correct the claims as follows:

2. An isolated NF2 transcript isoform, wherein the isoform is mouse NF2 transcript isoform II encoding a protein comprising the amino acid sequence depicted in [Figure 2 (SEQ ID NO:5)] Figures 2A-2C (SEQ ID NO:5).

3. An isolated NF2 transcript isoform, wherein the isoform is mouse NF2 transcript isoform III encoding a protein comprising the amino acid sequence depicted in [Figure 3 (SEQ ID NO:7)] Figures 3A-3C (SEQ ID NO:7).

Signed and Sealed this

Eleventh Day of November, 1997

Attest:

BRUCE LEHMAN

Attesting Officer

Commissioner of Patents and Trademarks